(12) United States Patent
Rigatti et al.

(10) Patent No.: US 8,399,192 B2
(45) Date of Patent: *Mar. 19, 2013

(54) USING POPULATIONS OF BEADS FOR THE FABRICATION OF ARRAYS ON SURFACES

(75) Inventors: Roberto Rigatti, Essex (GB); Geoffrey Paul Smith, Essex (GB); Jonathan Mark Boutell, Essex (GB)

(73) Assignee: Illumina Cambridge Limited, Walden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,562

(22) Filed: Feb. 3, 2012

(65) Prior Publication Data

US 2012/0172259 A1 Jul. 5, 2012

Related U.S. Application Data

(63) Continuation of application No. 12/497,397, filed on Jul. 2, 2009, now Pat. No. 8,198,028.

(60) Provisional application No. 61/077,844, filed on Jul. 2, 2008, provisional application No. 61/149,616, filed on Feb. 3, 2009.

(51) Int. Cl.
*C12Q 1/68* (2006.01)
*C12P 19/34* (2006.01)

(52) U.S. Cl. ............ 435/6.1; 435/7; 435/6.12; 435/91.2

(58) Field of Classification Search .................... 435/6.1, 435/7, 6.12, 91.2
See application file for complete search history.

(56) References Cited

U.S. PATENT DOCUMENTS

| | | |
|---|---|---|
| 5,604,097 A | 2/1997 | Brenner |
| 5,641,658 A | 6/1997 | Adams et al. |
| 5,795,714 A | 8/1998 | Cantor et al. |
| 5,800,992 A | 9/1998 | Fodor et al. |
| 5,830,645 A | 11/1998 | Pinkel et al. |
| 5,846,719 A | 12/1998 | Brenner |
| 6,013,445 A | 1/2000 | Albrecht |
| 6,023,540 A | 2/2000 | Walt et al. |
| 6,090,592 A | 7/2000 | Adams et al. |
| 6,251,691 B1 | 6/2001 | Seul |
| 6,306,597 B1 | 10/2001 | Macevicz |
| 6,327,410 B1 | 12/2001 | Walt et al. |
| 6,355,431 B1 | 3/2002 | Chee et al. |
| 6,406,848 B1 | 6/2002 | Bridgham et al. |
| 7,057,026 B2 | 6/2006 | Barnes et al. |
| 7,329,860 B2 | 2/2008 | Feng et al. |
| 7,425,431 B2 | 9/2008 | Church et al. |
| 7,427,673 B2 | 9/2008 | Balasubramanian et al. |

(Continued)

FOREIGN PATENT DOCUMENTS

| | | |
|---|---|---|
| EP | 0 392 546 | 10/1990 |
| WO | WO 01/32935 | 5/2001 |

(Continued)

OTHER PUBLICATIONS

Pammer et al., ChemPhysChem 6, 900-903 (2005).*

(Continued)

*Primary Examiner* — Kenneth R. Horlick
(74) *Attorney, Agent, or Firm* — Brent C. Moore

(57) ABSTRACT

The present invention provides a method of creating an array of features. The method can include steps of (a) providing a plurality of beads, wherein each bead in the plurality of beads includes probe content; (b) contacting the plurality of beads with a surface to produce a layer of beads on the surface; and (c) transferring the probe content from the beads to the surface to create an array of spatially discrete features on the surface, wherein each spatially discrete feature includes probe content from a bead in the plurality of beads.

27 Claims, 11 Drawing Sheets

U.S. PATENT DOCUMENTS

| | | |
|---|---|---|
| 7,485,428 B2 | 2/2009 | Armes et al. |
| 7,622,294 B2 | 11/2009 | Walt et al. |
| 2003/0108867 A1 | 6/2003 | Chee |
| 2003/0108900 A1 | 6/2003 | Oliphant et al. |
| 2003/0170684 A1 | 9/2003 | Fan |
| 2003/0204322 A1 | 10/2003 | Loehrlein et al. |
| 2003/0211489 A1 | 11/2003 | Shen et al. |
| 2003/0215821 A1 | 11/2003 | Gunderson et al. |
| 2004/0171053 A1 | 9/2004 | Hu |
| 2005/0042648 A1 | 2/2005 | Griffiths et al. |
| 2005/0079510 A1 | 4/2005 | Berka et al. |
| 2005/0130173 A1 | 6/2005 | Leamon et al. |
| 2005/0181394 A1 | 8/2005 | Steemers et al. |
| 2007/0087382 A1* | 4/2007 | Howorka et al. ............ 435/7.1 |
| 2007/0128624 A1 | 6/2007 | Gormley et al. |
| 2007/0231824 A1 | 10/2007 | Chee et al. |
| 2008/0003571 A1 | 1/2008 | McKernan et al. |
| 2008/0009420 A1 | 1/2008 | Schroth et al. |
| 2008/0242560 A1 | 10/2008 | Gunderson et al. |
| 2008/0262172 A1 | 10/2008 | Zhao |
| 2008/0262747 A1 | 10/2008 | Kain et al. |
| 2009/0062129 A1 | 3/2009 | McKernan et al. |
| 2009/0088327 A1 | 4/2009 | Rigatti et al. |
| 2009/0118128 A1 | 5/2009 | Liu et al. |
| 2009/0181370 A1 | 7/2009 | Smith |
| 2010/0111768 A1 | 5/2010 | Banerjee et al. |

FOREIGN PATENT DOCUMENTS

| | | |
|---|---|---|
| WO | WO 2004/018497 | 3/2004 |
| WO | WO 2004/067759 | 8/2004 |
| WO | WO 2005/010145 | 2/2005 |
| WO | WO 2005/065814 | 7/2005 |
| WO | WO 2005/082098 | 9/2005 |
| WO | WO 2006/058246 | 6/2006 |
| WO | WO 2007/010251 | 1/2007 |
| WO | WO 2007/010252 | 1/2007 |
| WO | WO 2007/123744 | 11/2007 |
| WO | WO 2007/135368 | 11/2007 |
| WO | WO 2008/041002 | 4/2008 |
| WO | WO 2008/076842 | 6/2008 |

OTHER PUBLICATIONS

Extended European Search Report from European Patent Application No. 09774581.4, dated Oct. 17, 2011.

Barbee, et al., "Magnetic Assembly of High-Density DNA Arrays for Genomic Analyses", Analytical Chemistry, 2008, A-F.

Drmanc et al., "Prospects for a Miniaturized, Simplified and Frugal Human Genome Project," Scientia Yugoslavica 16(1-2):97-107,1990.

Drmanc et al., "Sequencing by Hybridization (SBH) with Oligonucleotide Probes as an Integral Approach for the Analysis of Complex Genomes," International Journal of Genome Research 1(1):59-79, 1992.

Lin et al., "Replication of DNA Microarrays from Zip Code Masters," JACS Articles, 2006, A-E.

Schwartz et al., "High Density single molecule surface patterning with colloidal epitaxy," Applied Physics Letters 91: 083902-1-083902-3, 2007.

* cited by examiner

Testing method for cluster seeding:

- Use biotinylated primer in PCR
- Bind biotinylated PCR product to streptavidin coated beads of defined size (1 micron magnetic beads)
- Wash beads and use NaOH to make single stranded
- Flush into flowcell to hybridize to surface primers

Bead hyb of 2 different PE monotemplates

- Two different monotemplates, CT417 + CT418
- Different bases at 1st cycle
- PCR with one biotinylated primer

```
CT417      215bp, Insert: 90bp
AATGATACGGCGACCACCGAGATCTACACTCTTTCCCTACACGACGCTCTTCCGATCTCTCACTCCTGGCGAGACG
GACGTGTGACTAGGCATGGGCCCTTAGGTCTCCAGTTCCTGGGTTAGCTTGTATTTTTGAACATCTCCTGTATATTA
GTTAGATCGGAAGAGCGGTTCAGCAGGAATGCCGAGACCGATCTCGTATGCCGTCTTCTGCTTG CT418      180bp, Insert: 61bp
AATGATACGGCGACCACCGAGATCTACACTCTTTCCCTACACGACGCTCTTCCGATCTTCGCCCGGGAGAGTT
TCCGCGGAGGATGGGTTCGGTTTGAATCGGCGTTAAGGAAGAGAACATCGGAAGAGCGGTTCAGCAGGAATCCGA
GACCGATCTCGGTATGCCGTCTTCTGCTTG
```

- Purified with magnetic streptavidin beads
- Flushed in separately, or mixed and flushed in

*FIG. 4*

USING POPULATIONS OF BEADS FOR THE FABRICATION OF ARRAYS ON SURFACES

CROSS-REFERENCE TO RELATED APPLICATION

This application is a continuation of U.S. patent application Ser. No. 12/497,397, filed Jul. 2, 2009 which claims the benefit of U.S. Provisional Patent Application No. 61/077,844 filed Jul. 2, 2008 and U.S. Provisional Patent Application No. 61/149,616 filed Feb. 3, 2009, the disclosures of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480273_402a_SEQUENCE_LISTING.txt. The text file is 3 KB, was created on Sep. 29, 2009, and was submitted electronically via EFS-Web on Sep. 29, 2009, concurrent with the filing of a Response to Missing Parts in U.S. patent application Ser. No. 12/497,397.

FIELD OF THE INVENTION

The present invention relates to methods of fabricating analytical arrays. More specifically it relates to methods of using beads to deposit analytes onto a surface to form analyte features that are separated from each other at a desired spacing.

BACKGROUND TO THE INVENTION

The draft sequence of the human genome was published in 2001 by the Human Genome Consortium (*Nature* 409; issue 6822) and Celera genomics (*Science,* 291; 1304-1351), thus marking an important advancement to the genetics chapter for society. Capitalizing on this investment and realizing the potential of the Human Genome Project provides a better understanding of genetic variation and its effect in disease.

It has been estimated that any two copies of the human genome differ from one another by as little as 0.1%, in other words a total of three million variants, or one variant every 1000 bases, over a total of three billion that make up the human genome. Since such variation affects disease susceptibility and responses to drugs, it is advantageous to identify the genetic factors which contribute to biological variation. DNA sequencing is a fundamental tool enabling the screening of genes for such genetic mutations associated with disease. High throughput, high accuracy sequencing methods are therefore beneficial for screening the complete genome sequence of an animal in order to identify unique nucleic acid sequences which may indicate the presence of physiological or pathological conditions.

DNA sequencing of large and complex genomes is currently limited by cost. In order to accurately sequence a human genome to a depth of 15× coverage requires the generation of at least 45 billion bases of sequence. Even for highly parallel sequencing technologies with read lengths of hundreds of base pairs, many hundreds of millions of sequencing reads are typically obtained in parallel. These reads may be recorded on microscopy based platforms and may therefore involve the consecutive capturing of many thousands of images on an imaging device such a CCD camera with a finite number of pixels. In order to maximize the rate of output of sequencing information, efforts have been made to increase the ratio of bases sequenced per image (i.e., the ratio of bases/pixels). In general, array techniques that rely on the random distribution of features can suffer from a low ratio of bases/pixels, due to a high number of dark pixels with no features (for example, if the density of features is too diffuse), or a high number of pixels that carry multiple overlapping features of different sequence (if the density of features is too concentrated) or both (due to the random nature of feature placement). A more efficient use of the imaging pixels can be made if the features on the surface are tightly packed, non-overlapping and of similar size and intensity to each other.

The present invention provides methods of fabricating arrays of features that avoid low ratios of bases/pixels associated with many array fabrication methods while exploiting advantages of random feature fabrication. Thus, the presently disclosed invention embodiments provide, for example, ease of array fabrication, low cost of array fabrication, an increase in the amount of data generated using any of a variety of high throughput imaging platforms, and other related advantages.

SUMMARY OF THE INVENTION

The present invention provides according to certain embodiments a method of fabrication of an array of nucleic acid fragments by copying the templates attached to an array of beads. The beads are attached to a surface via hybridization to a primer on the surface, thereby specifically selecting the beads with the templates thereon. The invention also provides in certain embodiments methods for the fabrication of arrays by using beads to control the density of features on the array.

One embodiment of the invention involves a method for fabricating an array of nucleic acids on a surface. The method can include: (a) providing a surface having one or more primer oligonucleotides attached to the surface; (b) providing a pool of beads, wherein beads in the pool have a plurality of templates attached thereto, the plurality comprising multiple copies of a single nucleic acid template sequence; (c) arraying the beads onto the surface by hybridizing the templates to the primer oligonucleotides; and (d) extending the primers to produce copies of the templates attached to the surface. In particular embodiments, the primers are extended under conditions in which no more than one copy of each template molecule is produced. For example, single cycle extension conditions, in which intervening denaturation steps are not applied, can be used. Alternatively, the primers can be extended under conditions in which a particular template molecule is copied several times. For example, multiple cycles of extension and denaturation can be carried out such that a given template can be repeatedly primed and copied. Optionally, the beads can be removed from contact with the surface after the primers have been extended to produce the one or more copies of the templates attached to the surface.

Accordingly, in certain related embodiments the step (b) of providing a pool of beads comprises forming the pool of beads by amplifying the nucleic acid template sequence on the beads, thereby producing the plurality of templates; in certain further embodiments the amplifying is performed in an emulsion and in certain other further embodiments the amplifying is performed by bridge amplification using two or more primer oligonucleotides immobilized on the beads. In certain further embodiments a subset of at least 90% of the beads on the surface carry one or more copies of the single nucleic acid template sequence, and in certain other further embodiments a subset of at least 99% of the beads on the surface carry one or more copies of the single nucleic acid template sequence. In certain further embodiments one or more of the primer oligonucleotides is cleaved after the amplification to leave single stranded templates on the beads.

In certain other embodiments of the above described methods, a subset of at most 10% of the beads in the pool comprise the copies of the single nucleic acid template sequence, and in certain other embodiments a subset of at most 1% of the beads in the pool comprise the copies of the single nucleic acid template sequence. In another embodiment the copies of the templates attached to the surface that are produced in step (d) comprise a plurality of nucleic acid features on the surface, wherein each of the features covers less area of the surface than the area covered by each of the beads. In another embodiment the method further comprises removing the beads from the surface after the extending of the primers.

In certain other embodiments the templates amplified on the beads originate from a pool of chemically synthesized oligonucleotides. In another embodiment the method further comprises an additional step of sequencing the copies of the templates attached to the surface that are produced in step (d). In another embodiment the primer oligonucleotides are attached to spatially random locations on the surface. In another embodiment the primer oligonucleotides are attached to spatially ordered locations on the surface. In another embodiment the primer oligonucleotides are attached to the surface in a number per unit area that exceeds the number of the beads arrayed within the unit area of the surface. In another embodiment in step (d) the plurality of templates attached to the beads are each copied two or more times.

Also provided is a device including an array of beads on a surface wherein the beads are immobilized via hybridization to one or more oligonucleotide primers on the surface.

The invention further provides a composition including (a) an array of beads on a surface, wherein the beads are attached to template nucleic acids, wherein the surface is attached to oligonucleotide primers and wherein the beads are immobilized on the surface via hybridization of the template nucleic acids to one or more of the oligonucleotide primers, and (b) a nucleic acid polymerase that may be bound to hybrids formed between the template nucleic acids and the one or more oligonucleotide primers.

BRIEF DESCRIPTION OF THE DRAWINGS

FIG. 4 shows nucleic acid sequences for two template molecules used in an exemplary PCR reaction.

Figure 1:
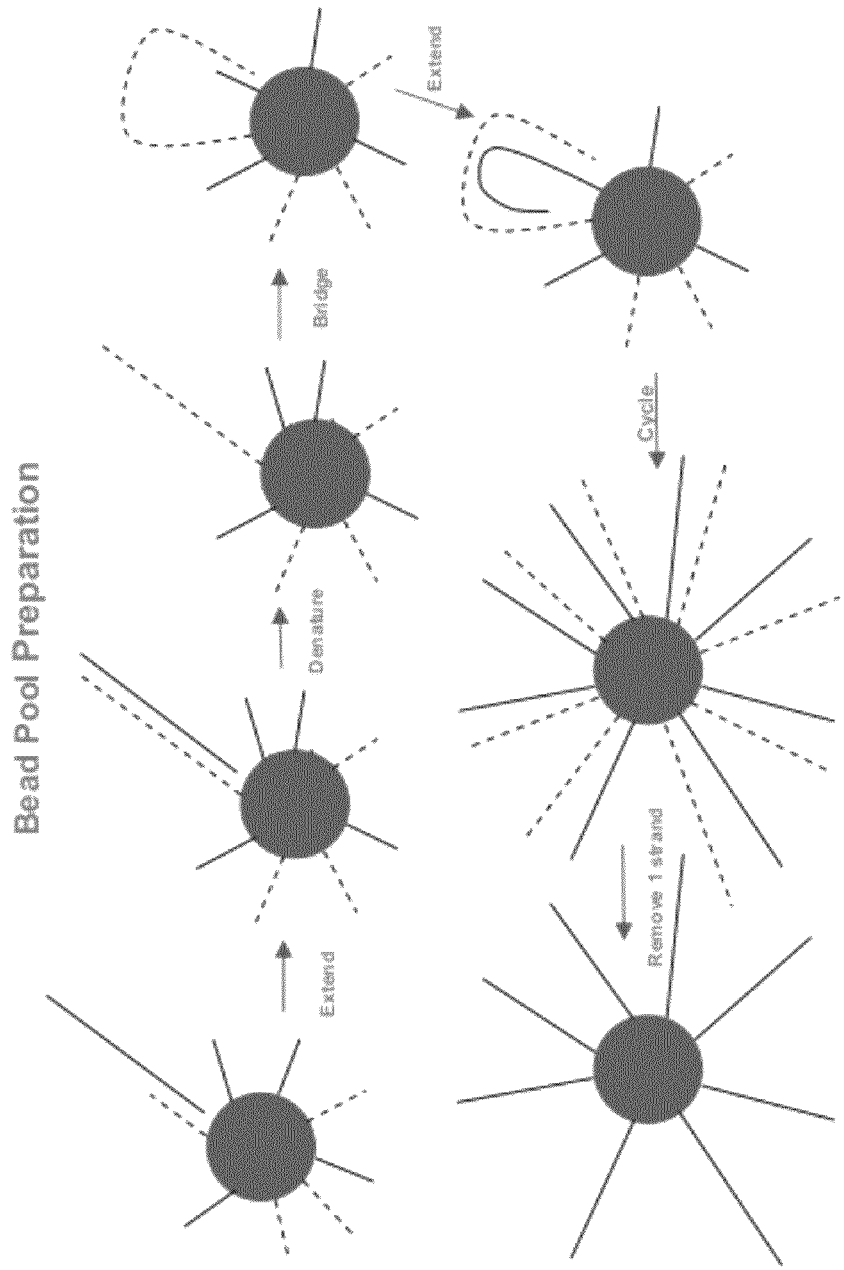
FIG. 1 shows a schematic of an embodiment of the invention where the templates are amplified onto beads.

All publications, patents, patent applications, or other documents cited in this application are incorporated by reference in their entirety for all purposes to the same extent as if each individual publication, patent, patent application, or other document were individually indicated to be incorporated by reference for all purposes.

DETAILED DESCRIPTION OF THE INVENTION

The present invention provides, according to certain herein disclosed embodiments, methods for creating an array of features on a surface based on content transferred from a plurality of beads to the surface. Content can be transferred in the form of one or more probe molecules that is physically transferred from a bead to a feature of the array. Content transfer can also be carried out by replicating a probe molecule from a bead to form a copy of the probe at a feature of the array or by synthesizing a probe at a feature on the array as directed by a catalyst or reagent present on a bead. The use of beads as a medium to transfer content to a surface allows an array of spatially discrete features to be formed on the surface. More specifically, a layer of beads can be contacted with a surface such that content present on the beads is transferred to the location of the surface that is closest to the bead. In this way the proximity of beads to each other in the layer determines the proximity of the features to each other on the surface. For example, transferring content from a tightly packed monolayer of spherical beads will produce an array of features that has a center-to-center spacing that is equivalent to the diameter of the beads. Accordingly, properties of the bead layer such as bead shape, bead size and bead packing density can be manipulated to obtain a desired pattern of features on an array.

In particular embodiments, the methods can be used to transfer or replicate one or more copies of a probe molecule from an individual bead to an individual feature of an array. An exemplary type of probe is a nucleic acid which can be copied from beads to form an array of nucleic acid probe features. More specifically, a population of beads, in which each bead carries a nucleic acid with a particular sequence, can be used to create features on an array surface, wherein each feature contains one or more copies of a particular nucleic acid sequence from a single bead in the population. Typically, each bead will have a single probe species present in one or more copies. Returning to the example of nucleic acid probes, each bead can have several copies (i.e., several nucleic acid molecules) with the same sequence (i.e., same species). Alternatively, a single copy of a nucleic acid probe can be transferred or replicated from a bead to a feature of an array. In addition to being useful as probes, the nucleic acids that are attached at features of the array can be used as primers or templates in any of a variety of array-based nucleic acid analyses.

It will be understood that a copy of a template nucleic acid made using a method set forth herein can have a sequence that is identical to the sequence of the template nucleic acid, the copy can have a sequence that is complementary to the sequence of the template nucleic acid, or both. Accordingly, the copy can be single stranded or double stranded. Similarly, the copy can be derived from a template that is double stranded or single stranded.

In particular embodiments, the present invention relates to a method of fabrication of an array of nucleic acid fragments by copying templates attached to a plurality of beads. The beads can be attached to the surface via hybridization to a primer on the surface, thereby specifically selecting the beads with the templates thereon.

Figure 8:
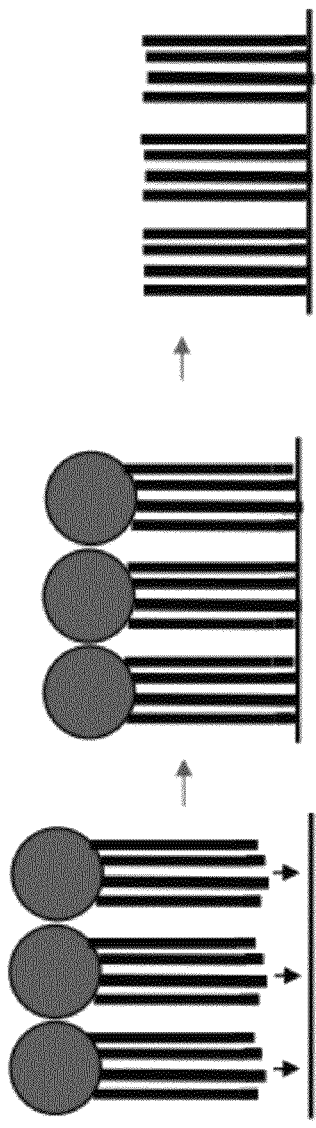
FIG. 8 shows a method of preparing features on a surface by physically transferring nucleic acid content from a layer of beads to the surface.

In particular embodiments, the beads may be prepared such that each bead carries one or more nucleic acid species, for example each bead may carry two amplification primers each having a different sequence. The nucleic acids may carry a reactive moiety which allows attachment of each nucleic acid to a surface. The beads may be spread out on the surface, and the moiety on each nucleic acid allowed to react to form a covalent bond with the surface. The beads can then be removed, for example by cleaving a linker that attaches each nucleic acid to the bead. In this way an array of nucleic acid features is produced on the surface where the density of features on the array is correlated with the size and/or spacing of the beads. The nucleic acids that are transferred from the beads to the surface can be single stranded (as shown for example in FIG. 8) or they can be double stranded.

Figure 9:
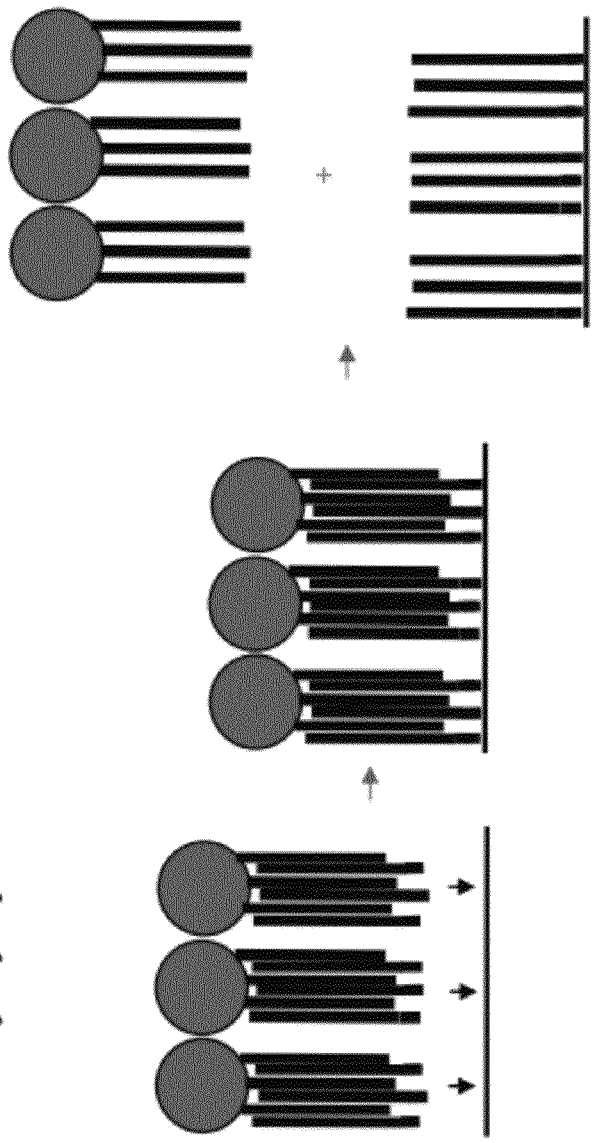
FIG. 9 shows a method of preparing features on a surface by physically transferring nucleic acid content from a layer of beads to the surface, wherein a single strand from each of several nucleic acid hybrids on beads is transferred to the surface.
Figure 10:
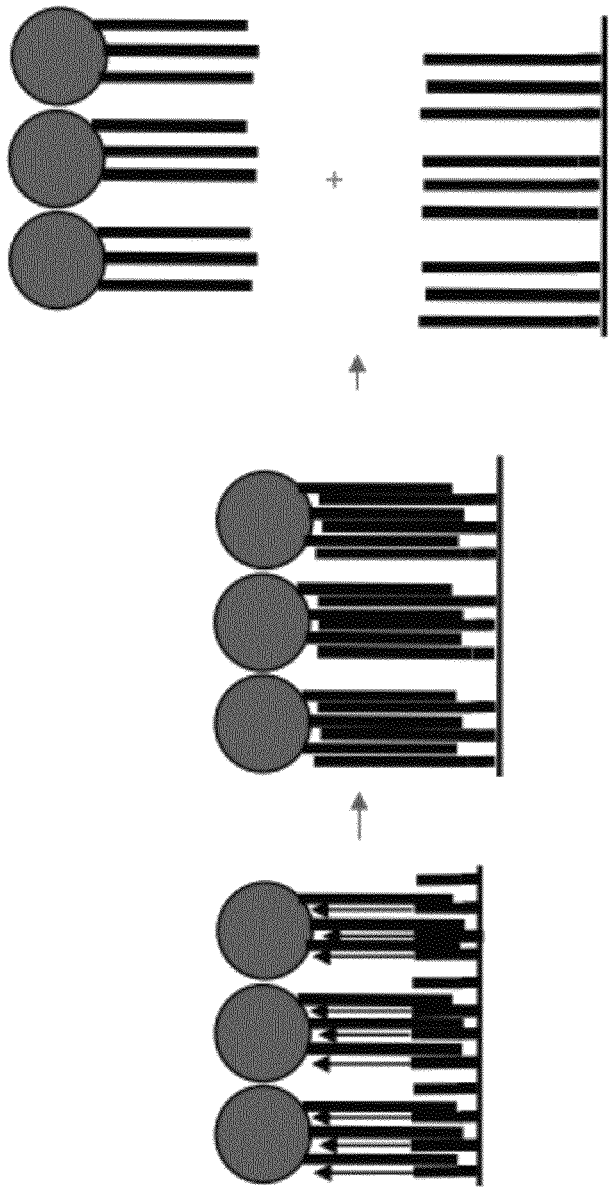
FIG. 10 shows a method of preparing features on a surface by copying nucleic acids from a layer of beads using extension of primers on the surface.

In embodiments wherein beads are attached to double stranded templates, one of the two strands in each template can be transferred to a surface. For example as shown in FIG. 9, beads having double stranded templates in which one strand comprises a reactive moiety can be arrayed on a solid support and the hybridized material reacted with the surface. The array is therefore fabricated by the transfer of one strand of the hybridized material from the beads to the surface, and the density of features is correlated with the size and/or spacing of the beads. The beads can be removed from the surface by denaturation, and can be re-used if desired by 'inking' with more hybridized material.

Figure 11:
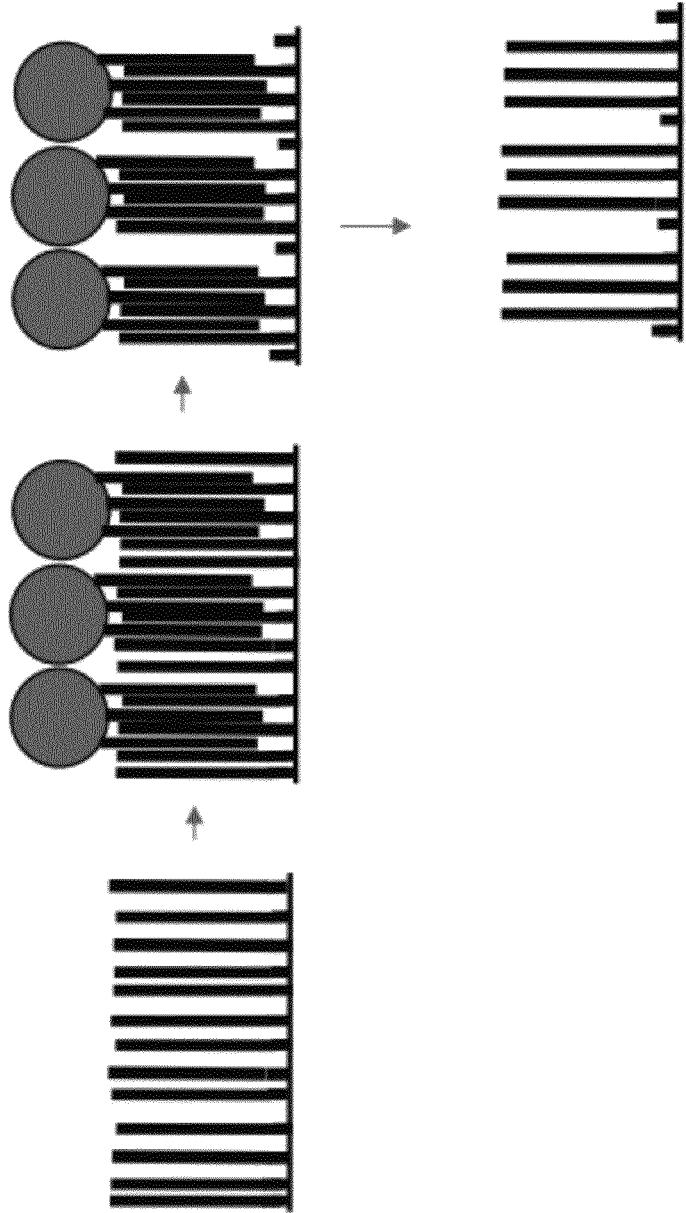
FIG. 11 shows a method of preparing features on a surface by digesting material not in contact with a bead in a layer of beads.

An array may also be fabricated using hybridization of one or more nucleic acids on beads to one or more primers on a surface and extension of the one or more primers using the one or more nucleic acids as templates. An exemplary diagram is shown in FIG. 11. For example, the beads may carry a nucleic acid having a sequence of e.g., 20 nucleotides. The surface may carry a complementary nucleic acid having a sequence of e.g., 8 or 12 nucleotides. The nucleic acids on the beads can therefore hybridize to the nucleic acids on the surface at low temperatures. The 20-mer nucleic acid sequences can be extended using a polymerase and nucleotide triphosphates such that the full length primers on the surface are only prepared where the beads are in contact with the support. Alternatively, the primers on the surface can be extended by ligation using an oligonucleotide complementary to the sequence on the beads. The array will have areas of full length sequences and shorter sequences and can be used for subsequent assays where features are only produced in regions of full length sequences. For example in the preparation of nucleic acid clusters by amplification, clusters can be isolated from each other because the short sequences are too short to enable bridge amplification, and hence the clusters can not cross the gaps between the islands of long sequences. In such examples, the template on the bead may be a synthesized oligonucleotide sequence. The template may, for example, comprise an artificial oligonucleotide sequence of between 20-50 base pairs.

Arrays may also be fabricated by using beads to either protect or activate certain regions of a surface. For example, content attached to one or more beads can bind to content present on a surface to selectively protect the content on the beads that is in contact with content on the surface, the content on the surface that is in contact with the content on the beads, or both, from degradation or modification. Alternatively or additionally, content attached to one or more beads can react with content present on a surface to selectively modify the content on the beads that is in contact with content on the surface, the content on the surface that is in contact with the content on the beads, or both. Taking as an example beads having one or more nucleic acid templates that are complementary to nucleic acid primers on a surface, the beads can be located on the surface and the surface treated with exonuclease under conditions wherein the beads offer protection from exonuclease treatment such that the primers can be selectively digested on the regions of surface between the beads.

As a further example, beads may carry an enzyme or other moiety that reacts with primers on a surface that are in contact with the beads. More specifically, the beads may carry a phosphatase to remove a phosphate group from primers at certain locations of the surface that are on contact with the beads, thereby forming features having dephosphorylated primers. Alternatively the beads may carry an exonuclease or endonuclease to digest the surface bound primers that come into contact with the beads such that regions that do not come into contact with the beads form features having full length (i.e., non-digested) primers. The dephosphorylated primers, or full length primers at the respective features can then be used to produce nucleic acid clusters, whereas the phosphorylated, or shortened primers are not amenable to further extension. Alternatively the beads may carry a chemical reagent such as a phosphine which induces a chemical modification to the primers on the surface. In the cases of beads carrying reagents to alter the surface bound primers, the beads may also carry nucleic acid sequences which hybridize to the surface, thus causing the beads to be immobilized onto the surface rather than simply diffusing in solution.

As used herein, the term "array" means a population of different probe molecules that are attached to a surface such that the different probe molecules can be differentiated from each other according to relative location. An individual feature of an array can include a single copy of a probe molecule or multiple copies of the probe molecule can be present as a population of probes at an individual feature of the array. The population of probes at each feature typically is homogenous, having a single species of probe. Thus, multiple copies of a single nucleic acid sequence can be present at a feature, for example, on multiple nucleic acid molecules having the same sequence. However, in some embodiments a heterogeneous population of probes can be present at a feature. Thus, a feature may but need not include only a single probe species and can instead contain a plurality of different probe species such as a mixture of nucleic acids having different sequences.

Neighboring features of an array can be discrete one from the other in that they do not overlap. Accordingly, the features can be adjacent to each other or separated by a gap. In embodiments where features are spaced apart, neighboring sites can be separated, for example, by a distance of less than 100 µm, 50 µm, 10 µm, 5 µm, 1 µm, 0.5 µm or less. The layout of features on an array can also be understood in terms of center-to-center distances between neighboring features. An array useful in the invention can have neighboring features with center-to-center spacing of less than about 100 µm, 50 µm, 10 µm, 5 µm, 1 µm, 0.5 µm or less. Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

The methods set forth herein can be used to make arrays having features at any of a variety of densities. Very high density arrays are useful in the invention including, for example, those having from about 10,000,000 features/cm$^2$ to about 2,000,000,000 features/cm$^2$ or from about 100,000,000 features/cm$^2$ to about 1,000,000,000 features/cm$^2$. High density arrays include, for example, those in the range from about 100,000 features/cm$^2$ to about 10,000,000 features/cm$^2$ or about 1,000,000 features/cm$^2$ to about 5,000,000 features/cm$^2$. Moderate density arrays range from about 10,000 features/cm$^2$ to about 100,000 features/cm$^2$, or from about 20,000 features/cm$^2$ to about 50,000 features/cm$^2$. Low density arrays are generally less than 10,000 features/cm$^2$ with from about 1,000 features/cm$^2$ to about 5,000 features/cm$^2$ being useful in particular embodiments. Very low density arrays having less than 1,000 features/cm$^2$, from about 10 features/cm$^2$ to about 1000 features/cm$^2$, or from about 100 features/cm$^2$ to about 500 features/cm$^2$ are also useful in some applications.

As used herein, the term "surface" means a part of a support structure that is accessible to contact with reagents, beads or analytes. The surface can be substantially flat or planar. Alternatively, the surface can be rounded or contoured. Exemplary contours that can be included on a surface are wells, depressions, pillars, ridges, channels or the like. Exemplary materials that can be used as a support structure include, but are not limited to, glass such as modified or functionalized glass; plastic such as acrylic, polystyrene or a copolymer of styrene and another material, polypropylene, polyethylene, polybutylene, polyurethane or Teflon™; polysaccharides or cross-linked polysaccharides such as agarose or Sepharose; nylon; nitrocellulose; resin; silica or silica-based materials including silicon and modified silicon; carbon-fibre; metal; inorganic glass; optical fibre bundle, or a variety of other polymers. A single material or mixture of several different materials can form a surface useful in the invention.

A surface used in the invention may be contained in a flow chamber allowing convenient movement of liquids across the surface to enable the transfer of reagents. Exemplary flow cells that can be used are described in WO 2007/123744, which entered the U.S. national phase as U.S. patent application Ser. No. 12/295,337, each of which is incorporated herein by reference.

As set forth herein, transfer of content from beads to a surface can occur due to interaction of the surface with the content on the beads. Thus, the surface can include moieties or groups that interact with the content on beads that is to be transferred. The interactions can be covalent or non-covalent in nature. For example, the surface can include reactive groups that will form a covalent bond with reactive groups on the beads. Some useful reactive groups and reactions for forming covalent bonds are set forth in further detail below in regard to attaching nucleic acids to surfaces or beads. In embodiments wherein transfer of content from beads to a surface occurs via non-covalent interactions, the surface can include groups or moieties such as nucleic acids having sequences that are complementary to sequences of nucleic acids on the beads, ligands having affinity for receptors on the beads or receptors having affinity for ligands on the beads. Exemplary receptor-ligand pairs that can be used include without limitation antigen and immunoglobulin or active fragments thereof, such as FAbs; immunoglobulin and immunoglobulin (or active fragments, respectively); avidin and biotin, or analogues thereof having specificity for avidin such as imino-biotin; streptavidin and biotin, or analogues thereof having specificity for streptavidin such as imino-biotin; and carbohydrates and lectins.

Once content has been transferred from beads to a surface by covalent or non-covalent attachment of the content bearing material to the surface, the material can be detached from the beads. Detachment can be carried out by a method that is appropriate for the type of bead attachment. For example a non-covalent attachment to beads can be disrupted using denaturation methods or conditions that prevent the non-covalent interactions. In embodiments that utilize covalent attachment of material to beads the material can be cleaved from the beads using chemical cleavage, enzymatic cleavage, photolysis or the like.

Nucleic acids can be immobilized to a bead or other surface by single point covalent attachment to the surface at or near the 5' end of the nucleic acid. In embodiments where the nucleic acid serves as a primer, attachment is configured to leave the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, for example, located at the 5' end. In the case of solid-supported polyacrylamide hydrogels (as described below), this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described fully in U.S. application Ser. No. 10/585,373, deriving from WO05065814, the contents of which are incorporated herein by reference in their entirety. Attachment can also occur via ligand receptor interactions such as those set forth elsewhere herein. Hydrogel surfaces are especially advantageous for the transfer of material from the bead to the surface. A porous, flexible hydrogel surface, where the beads can embed into the surface, can allow transfer of higher amounts of material from the bead to the hydrogel due to the increased surface-surface contact area as compared to the surface area available for a rigid planar surface.

Certain embodiments of the invention may make use of solid supports or beads comprised of an inert substrate or matrix (e.g., glass slides, polymer beads, etc.) which has been "functionalized", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g., polynucleotides) may be directly covalently attached to the intermediate material (e.g., the hydrogel), but the intermediate support material may itself be non-covalently attached to the substrate or matrix (e.g., the glass substrate). It will be understood that a solid support that is useful in the invention can have several layers and that the layers can have different compositions.

Any of a variety of methods can be used to prepare a surface for use in a method of the invention. Such methods can be used to deposit groups or moieties uniformly across all or part of a surface. In some embodiments, groups or moieties can be attached in a particular pattern. However, typically patterned deposition of groups and moieties on a surface to be used for bead-based transfer is not necessary because bead transfer is used to create a pattern of features on the surface.

In particular embodiments groups or moieties are present on a surface at a density that exceeds the density attainable by a monolayer of beads that are contacted with the surface. For example, in embodiments where template-bearing beads are contacted with a surface having attached primers, the primers can be attached to the surface at a higher density than the density of beads that contact the surface such that each bead is proximal to a plurality of the surface-attached primers. Thus a plurality of templates on each bead can hybridize to a plurality of primers on the surface. A plurality of surface-attached primers that is proximal to each individual bead can be, for example, at least 2; 10; 100; 1,000; 10,000; 100,000 or more primers depending upon the size of the bead and density of primers on the surface. Accordingly, a plurality of templates that is copied to a feature can be at least 2; 10; 100; 1,000; 10,000; 100,000 or more templates. Similar densities can be used for other moieties used for transfer of other materials from beads in a method of the invention according to certain embodiments.

As used herein, the term "bead" means a small body made of a rigid or semi-rigid material. The body can have a shape characterized, for example, as a sphere, oval, microsphere, or other recognized particle shape whether having regular or irregular dimensions. Exemplary materials that are useful for beads include, without limitation, glass such as modified or functionalized glass; plastic such as acrylic, polystyrene or a copolymer of styrene and another material, polypropylene, polyethylene, polybutylene, polyurethane or Teflon™; polysaccharides or cross-linked polysaccharides such as agarose or Sepharose; nylon; nitrocellulose; resin; silica or silica-based materials including silicon and modified silicon; carbon-fiber; metal; inorganic glass; optical fiber bundle, or a variety of other polymers. Exemplary beads include controlled pore glass beads, paramagnetic beads, thoria sol, Sepharose beads, nanocrystals and others known in the art as described, for example, in Microsphere Detection Guide from Bangs Laboratories, Fishers Ind. Beads can be made of biological or non-biological materials. Magnetic beads are particularly useful due to the ease of manipulation of magnetic beads using magnets at various steps of the methods described herein.

The invention provides methods that allow for the transfer of material from a bead to a surface. Any of a variety of materials can be present on a bead and used for transfer including, for example, the groups and moieties set forth above in regard to surfaces. Similarly the methods set forth above for preparing surfaces can be used to functionalize beads for use in the methods of the invention. The use of template nucleic acids on the beads to hybridize to surface-attached primers allows efficient capture of the beads, such that any beads that lack templates can be removed since they will not hybridize. In particular embodiments, the beads are captured to form a single layer, the primers hybridized to the templates are extended, and the beads are removed after the primer extension reaction has occurred. In such embodiments, the extended primers on the surface are derived from the beads, and therefore the features produced may have minimal overlap with each other.

Using the bead-based transfer methods set forth herein, each feature generated on the surface of an array can be of similar or smaller size than the area of the surface occupied by the bead from which the feature was produced, and all the features will typically be of similar size and intensity to each other. The uniform size, uniform intensity and lack of overlap can provide a usable density of features per unit area that is higher than that obtainable from other random deposition methods since these other methods often give rise to a surface where the features may be overlapping and of different sizes and intensities. Images of tightly packed non overlapping arrays with features of uniform size and intensity are typically easier to analyze than images where a subset of the features overlap with each other.

Accordingly, the methods set forth herein provide several advantages not provided by other random deposition methods. In this regard it will be understood that there are at least two types of order for an array described herein, the first relating to the spacing and relative location of attachment sites and the second relating to identity or predetermined knowledge of the particular species of molecule that attaches at a particular site. An array fabricated using the methods set forth herein can be ordered in one respect and random in another. For example, in several embodiments set forth herein a substrate is contacted with a population of nucleic acids under conditions where the nucleic acids attach at sites that are ordered with respect to their relative locations but random with respect to knowledge of the sequence for the nucleic acid species present at any particular site. Accordingly, features of an array can be randomly located such that nearest neighbor features have random spacing between each other. Alternatively the spacing between features can be ordered, for example, forming a regular pattern. In another respect, features of an array can be random with respect to the identity or predetermined knowledge of the species of analyte that occupies each feature independent of whether spacing produces a random pattern or regular pattern.

Beads exposed to the surface of an array substrate in a method according to certain embodiments of the invention may be present as a mixture of beads with and without nucleic acid molecules attached. The nucleic acid molecules may include attached primers and/or templates. Depending upon the methods used to prepare the beads and amplify the templates there may be beads with no nucleic acid molecules at all, beads with primers and no template, beads with both primers and nucleic acid templates, or even beads that carry only templates due to the conversion of all the primers to templates in an amplification reaction. The surface to which the beads are to be contacted for transfer of template sequences may have attached primers that are complementary to the ends of the templates such that the beads are captured onto the surface via hybridization to the templates. Removal of the beads without templates which do not hybridize allows the ratio of beads with templates to beads without templates to be different from the ratio of the beads in the mixture that was initially applied to the surface. The beads in solution without templates can therefore be removed simply by removing the solution. Optionally, the array surface can subsequently be washed under conditions where nucleic acid hybrids between bead-bound templates and primers on the array surface are maintained whereas beads that do not interact with the surface or those having only non-specific interaction with the surface are removed.

In particular embodiments, beads having templates that are complementary to primers on a surface can be selectively immobilized to the surface while beads without templates can be removed due to the selective hybridization conditions. Beads having attached templates will be retained on the surface by hybridization of the templates to the primers. Beads without attached templates will not be retained and can be washed away such that the majority of the beads on the surface have a template attached. For example, greater than 90% of the beads immobilized on the surface may carry a template, or even greater than 99% of the immobilized beads may carry a template.

In particular embodiments, beads are captured to a surface as a single layer. An advantage of capturing beads as a single layer is that the nucleic acid template features on the surface are at a uniform focal depth, and at a single 'monolayer' depth of beads on the surface. The use of the templates on the beads to affect capture by hybridization allows the beads to be captured to form a tightly packed array of beads, and the beads which are physically held above the surface are not captured, thus forming a bead monolayer on the surface. The phrase "captured to a single layer" therefore means that the beads are held on the surface at a depth approximating only a single bead. In other words, beads captured to a single layer will be held on the surface in a layer having a depth that is no greater than the diameter of the beads. Typically, when beads are captured to a single layer the number of beads immobilized on the surface will be less than or equal to the number of beads that would theoretically fit into that area of surface.

The features on a surface may be fabricated using the methods set forth herein such that the features do not overlap with each other. Content transferred from a bead to a surface will typically occupy a discrete location of the surface that is proximal to the bead. Thus the features that come from one bead typically will not merge into features coming from a different bead. Accordingly, the images seen on the surface will show discrete features, the size and shape of which will mirror the size and shape of the beads in a monolayer when viewed from above. For example, if the beads used to transfer content to a surface are spherical, then the features on the surface will appear as circles. In contrast, features that are merged together may appear as ovals or figures of eight. Following bead-based transfer there may be one or more dark pixels between one feature and the next. The images may be constructed such that each feature occupies a single pixel, or a square of pixels (e.g., 4, 9, 16, etc.), with no dark pixels between features. One advantage of non-overlapping arrays over overlapping arrays is the ability to reduce the number of pixels between images. In particularly useful embodiments, the number of features will mirror the number of pixels on the detector, and hence the imaging is 100% efficient in terms of features per pixels. Non-overlapping features therefore include those in which the template sequence, transferred to a surface from one bead does not become intermingled with the template sequence, from a different bead.

As set forth above, the features on the surface of an array can originate from a bead in solution. The features may be copied or transferred from the beads to the surface. As the copying or transferring utilizes molecular contact between the beads and the surface, the area of the surface to which the bead is able to interact will typically be similar or less than the size of the beads. Thus each feature on the surface can be of similar or smaller size compared to the cross-sectional area of the beads. The beads may be spherical in size, in which case this can be described in terms of diameter, or may be other shapes, in which case this can be described in terms of area. The area of the surface covered by the features will typically be no greater than the area of the surface covered by the bead.

In particular embodiments, features on a surface which originate from beads will be of similar size to each other. Variation between the sizes of the features will typically reflect the variation in the sizes of the beads. Accordingly, a spherical bead pool with a diameter of 1 micron plus/minus 25% typically gives circular features on a surface that are on average 1 micron diameter but varying in diameter by 25%. The variation in area between the different features may, for example, be less than 25%, or less than 10%, or less than 5%, or less than 1%. If desired, arrays having a larger variation in feature area can be fabricated.

Features on a surface that are transferred from beads may be smaller than the area of the surface that is (or was) occupied by the beads. The density of beads, and therefore features, may be tightly packed. The density of beads may, for example, be at least 50% of the available surface area, or at least 60% of the available surface area, or at least 70% of the available surface area, or at least 80% of the available surface area or more. The beads may be disposed in a flow chamber in a closely packed planar array. As used herein, "closely packed" in reference to a pool of spherical beads in contact with a surface, means that the number of spherical beads per unit area in a layer of the pool that is adjacent to the surface is at least eighty percent of the number of the spherical beads in a hexagonal array of equal area. As used herein, a "hexagonal" array of spherical beads means an array of spherical beads in which every bead in the array contacts six other adjacent beads of the array.

Typically, the average distance between centers of adjacent beads in a closely packed pool of beads is less than two bead diameters or bead widths. If desired, closer packing can be used such that the average distance between centers of adjacent beads is less than one and a half bead diameters or bead widths. However, more diffuse packing is also possible. For example, the average distance between centers of adjacent beads in a pool of beads can be less than 3, 4, 5, or 10 bead diameters or bead widths. More diffuse packing can be achieved, for example, by including blank beads into a monolayer of content-bearing beads. Locations in the monolayer occupied by blank beads will be incapable of transferring content. Thus, the locations on the surface that are proximal to the blank beads will be devoid of content-bearing features. For example, in embodiments wherein templates are copied from beads to a surface, addition of blank beads to the layer of template-bearing beads that contact the surface will reduce the density of features copied to the surface.

In particular embodiments it is desired that upon labelling, different features on a surface which originate from different beads should incorporate a similar number of labels, and thus be of similar intensity to each other when imaged. As set forth above, conditions for transfer of template sequences from beads to a surface can be selected to provide features having uniform average area. Uniform labelling conditions can be used such that the number of molecules copied or transferred from the bead to the surface reflects the intensity of the features on the surface when each of the molecules is labelled. The intensity of the features may therefore fall within a narrow distribution. For example, the variations between the brightest and weakest feature may be less than 50%, or less than 25%, or less than 10% or less than 5% or less than 1%.

An embodiment of the invention may include a step of attaching nucleic acid templates to a population of beads, for example, prior to using the beads to fabricate an array. The templates may be present in solution and captured onto the beads, amplified in the presence of the beads, or amplified on the beads. The amplification on the beads may be done using an immobilized primer and a primer in solution, or with one or more immobilized primers via bridge amplification. Bridge amplification can be carried out under conditions wherein primers that participate in amplification are not provided in solution. The templates may be modified so that the ends of the templates carry universal sequences such that several different templates can be amplified using the same universal primers. Examples of methods of attaching universal ends to a collection of target fragments can be found in US application US 2007-0128624, the contents of which are incorporated herein by reference in their entirety.

Templates may be amplified on beads, in which case the method of amplification dictates the configuration of the primers on the beads. In order to use emulsion-based amplification techniques with a single template per emulsion bubble, a single primer is attached to the bead, and a single primer is in solution, thereby amplifying the templates such that one end of the duplex is attached to the bead. The hybridized strand can be removed by denaturing the duplex, thereby leaving the immobilized single strand on the bead. The single stranded templates can be captured onto a surface via primers complementary to the templates. Exemplary emulsion-based amplification techniques that can be used in a method of the invention are described in US 2005/0042648; US 2005/0079510; US 2005/0130173 and WO 05/010145, each of which is incorporated herein by reference.

Alternatively templates that are attached to beads may be amplified using bridge amplification on the beads, in which case all primers used for amplification are immobilized on the beads. An exemplary bridge amplification method is shown in FIG. 1. Typically, bridge amplification is carried out in conditions wherein there is no nucleic acid material in solution, thereby avoiding transfer between beads during the amplification cycles and cross-contamination of the beads. The templates can be prepared to have a moiety which allows direct attachment of the templates to the beads, for example a biotin moiety or a chemical species such as a thiophosphate or amino group. Alternatively, as shown in FIG. 1, the templates can be hybridized to primers on the beads and the primers extended followed by removal of the originally hybridized templates. Bridge amplification gives a double stranded template where both ends are immobilized. In order to obtain a single stranded template suitable for hybridization, one of the strands can be cleaved from the surface. The cleavage may be a chemical treatment of a suitable modified strand, for example periodate treatment of a primer carrying a diol modification, or reduction of a primer carrying a disulfide, or may be an enzymatic treatment, for example using a restriction endonuclease, or an enzyme treatment to produce an abasic nucleotide site followed by strand scission. Such treatments may be carried out on primers with a uracil modification using uracil DNA glycosylase and an endonuclease, or on primers with an 8-oxo guanine modification using FPG (formamidopyrimidine-DNA glycosylase). In cases where specific nucleotides are used in the cleavage, the nucleotides may be introduced to the surface primers as part of the extension reaction opposite the templates on the bead. Thus the extension reaction may be carried out using, for example, dUTP or 8-oxodGTP to introduce sites for linearization which are specific to the extended strands rather than universal across all the primer sequences attached to the support. Methods of bridge amplification that include steps to remove one strand of a duplex after bridge amplification are described in co-pending application published in the PCT as WO/2007/010251, the US national phase application of which published as US 2009/0118128, the contents of which are incorporated herein in their entirety.

In methods where templates are amplified on beads, it is advantageous to reduce the number of beads which carry multiple templates of different sequence, thereby enriching for beads having only a single template molecule attached. This may be achieved by using an excess of beads to template molecules during an amplification or attachment step, thereby ensuring the majority of the beads have no templates molecules at all. If the beads are present at a 9/1 excess over template nucleic acid molecules, then the probability is that 90% of the beads will carry no template, and only 1% of the beads will carry two templates. If the beads are present at a 99/1 excess, then 99% of the beads will probably carry no template, and only 0.01% of the beads will probably carry two templates.

The terms 'target nucleic acid sequence', 'target nucleic acid molecule', 'target nucleic acid' and 'target nucleic acid fragment' may be used interchangeably to refer to nucleic acid molecules or sequences that it is desired to sequence or otherwise analyze. A target nucleic acid can be attached to an array using the bead transfer methods set forth herein. Alternatively, a probe nucleic acid can be attached to an array by bead transfer methods and the array used subsequently to detect a target in a sample that interacts with the probe. In this regard, it will be understood that the terms "target" and "probe" can be used interchangeably with regard to nucleic acid detection methods, unless indicated to the contrary. The nucleic acid target may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample. The primary nucleic acid from which targets are derived can first be randomly fragmented. The targets can be processed into templates suitable for amplification by the placement of universal amplification sequences at the ends of each target fragment. The targets can also be obtained from a primary RNA sample by reverse transcription into cDNA. Templates may include any nucleic acid sequence capable of being copied by extending a primer. Templates may derive from biological sources, or be synthesized as oligonucleotides. Templates will generally have a region of known sequence such that a primer can be hybridized at a specific location on the template strand.

As used herein, the term 'nucleic acid' refers to deoxyribonucleic acid (DNA), ribonucleic acid (RNA), analogues of either DNA or RNA made from nucleotide analogs and the like. The term is applicable to single stranded (such as sense or antisense) and double stranded polynucleotides. The term as used herein also encompasses cDNA, that is complementary or copy DNA produced from an RNA template, for example by the action of reverse transcriptase.

Primary target nucleic acid molecules that are attached to a bead for transfer to a surface may have originated in double-stranded DNA (dsDNA) form (e.g., genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of certain embodiments of the invention using standard techniques well known in the art. The precise sequence of the primary nucleic acids molecules may be known or unknown.

In a particular embodiment, the primary target and/or template nucleic acid molecules are DNA molecules. More particularly, the primary target and/or template nucleic acid molecules represent the entire genetic complement of an organism, and are genomic DNA molecules which include both intron and exon sequences (coding sequence), as well as non-coding regulatory sequences such as promoter and enhancer sequences. Although it is also possible that particular sub-sets of nucleic acid sequences or genomic DNA can be used, such as, for example, particular chromosomes. Yet more particularly, the sequence of the primary nucleic acid molecules need not be known. Still yet more particularly, the primary nucleic acid molecules are human genomic DNA molecules. The DNA target molecules may be treated chemically or enzymatically, either prior to or subsequent to any random fragmentation processes, and prior to or subsequent to the ligation of adaptor sequences to target nucleic acid molecules. In the methods described herein, the nucleic acid samples may be fragmented prior to hybridization on beads, or may be used without fragmentation, and may be used with and without adapters. The samples may be subjected to amplification prior to use, for example, a whole sample amplification technique such as random primer extension.

Random fragmentation refers to reducing the length of a nucleic acid molecule in a non-ordered fashion, for example, by enzymatic, chemical or mechanical means. Such fragmentation methods are known in the art and can utilize standard methods (Sambrook and Russell, Molecular Cloning, A Laboratory Manual, third edition). Moreover, random fragmentation is designed to produce fragments irrespective of the sequence identity or position of nucleotides comprising and/or surrounding the break. More particularly, the random fragmentation is by mechanical means such as nebulization or sonication to produce fragments of about 50 base pairs in length to about 1500 base pairs in length, still more particularly 50-700 base pairs in length, yet more particularly 50-400 base pairs in length.

A nucleic acid used in a method of the invention, such as a template that is to be transferred from a bead to a surface, can include a universal sequence. The term "universal sequence" means a region of sequence that is common to two or more nucleic acid molecules where the molecules also have regions of different sequence. A universal sequence present in different members of a collection of molecules can allow the replication or amplification of multiple different sequences using a single universal primer complementary to the universal sequence. Thus a universal primer includes a sequence that can hybridize specifically to a universal sequence. The nucleic acid target molecules may be modified to attach universal adapters to one or both ends of the different target sequences, the adapters providing sites for hybridization of universal primers.

At least a portion of a universal primer will be complementary to the universal sequence to which it hybridizes. Thus universal adapter sequences attached to the ends of double stranded target fragments may carry a region of non complementary sequence. This non-complementary sequence can be used to hybridize a priming sequence, which can be used to copy one of the target strands. The primer may carry a tailed overhang, such that the 3' end of the adapter may also be extended complementary to the tailed primer. This tailed nature of the primer can be configured to allow selective introduction of a sequence at one end of the template strands, and can make the 3' and 5' ends of the templates different to each other and non-complementary to each other. The template strands may be amplified in solution prior to amplification on beads in order to generate a library of templates of different sequence comprising common 3' ends and common 5' ends.

A template library made by methods set forth herein or other methods known in the art may be attached to a pool of beads. The templates may be prepared in solution and attached to the beads, for example if the beads carry different nucleic acid sequences to selectively capture the templates. The nucleic acid sequences may be synthesized on the beads, or may be prepared and attached to the beads post synthetically. Each bead can carry a single sequence to enable emulsion-based PCR amplification, or each bead can carry two or more sequences to enable bead-based bridge amplification. The nucleic acid sequences may be attached covalently, for example using an amino modified nucleic acid and a carboxylate bead, or non-covalently, for example using biotin-modified nucleic acids and streptavidin beads. Bead-based bridge amplification of specific sequences is described in U.S. Pat. No. 6,090,592 and U.S. Pat. No. 5,641,658, the contents of which are incorporated herein by reference in their entirety.

Amplification of immobilized nucleic acids may be carried out by any known technique. Known techniques include thermocycling, where the temperature of a solution is altered to cycle between primer hybridization, extension and denaturation or isothermal amplification wherein the temperature is unchanged through the amplification reaction. Isothermal amplification techniques include cycles of buffer exchange with a denaturant such as formamide or hydroxide, and an extension mix comprising a polymerase and nucleoside triphosphates, as described in US 2008/0009420, the contents of which are incorporated herein in their entirety, or methods where the amplification is performed in a single solution which comprises, for example, a helicase or strand-displacing polymerase.

If desired, templates on beads may be amplified using helicase dependent amplification techniques. In methods of bridge amplification on beads, it may be advantageous to force as many primers as possible on the bead to be extended. As the original template is only present as a single copy, this may require a large number of cycles of amplification. Rather than performing hundreds of cycles of denaturation, renaturation and extension, the use of a helicase to denature the double strands, and a polymerase in combination in a single reagent composition, means that the beads can simply be left for a period of time and the bridge amplification allowed to proceed at a single temperature, without changing the reagents or having to separate the beads from the solution. Thus the beads can simply be left to extend all the primers on the surface rather than having to vary the conditions or manipulate the beads. Therefore certain embodiments of the invention include the use of helicase dependent amplification for amplifying single templates on beads. Helicase amplification methods can similarly be used to amplify nucleic acid sequences on a surface, for example, after being transferred from beads. An alternative method to amplify the templates on the beads is Recombinase Polymerase amplification (RPA) whereby a recombinase enzyme is used to anneal a second primer once the first primer has been extended. RPA is more fully described in U.S. Pat. No. 7,485,428, the contents of which are incorporated herein by reference in their entirety.

Beads may be prepared such that all the beads in a pool carry primers having the same sequence(s). If template nucleic acids are modified to carry universal ends, which may be complementary to the sequences of the primers attached to the beads, then the sequences on the beads can be used to amplify the templates. The primers may be synthesized on the beads, or may be attached post-synthetically. For example, primers may carry a biotin moiety for attachment to a streptavidin bead, or an amino functionality for attachment to a carboxylate bead. Any attachment method used to attach primers or other analytes to the beads is within the scope of these and related invention embodiments providing the attachment remains stable during the processes of the invention embodiments. Exemplary attachment methods and groups that can be used for modifying beads include, but are not limited to, those exemplified previously herein with regard to surface functionalization.

Alternatively, in certain embodiments the beads may be constructed such that different beads carry different primers. A patterned surface created using such beads will give patches of primers such that adjacent patches comprise primers of different sequence. Upon amplification using the primers on the support, it is possible that the templates being amplified can cross between adjacent patches, or features, if the patches are close together and the templates carry universal ends complementary to the patches. It is possible to increase the occupancy of the patches whilst reducing the number of patches carrying two different amplified templates if the patches comprise different sequences and the templates carry a number of universal ends. Nucleic acids will not spread between features in typical embodiments if the ends of the templates in one feature are not complementary to the primer sequences present in the adjacent feature. The use of said multiple non-hybridizing template ends and features with multiple different sequences is therefore advantageous in fabricating amplified arrays having a high density of features.

Beads used in certain embodiments of the invention may be of a diameter, width or length from 0.1 µm to 100 µm. Bead size can be selected to have reduced size, and hence get more features per unit area, whilst maintaining sufficient signal (template copies per feature) in order to analyze the features. The beads may be spherical, cylindrical, cubic or other three dimensional shape. The beads may be approximately 0.5-5 microns in size, or may be reduced further in size, for example, if desired to approach the optical resolution of the instrument used for imaging the features. The beads may be at most 0.5 micron, 0.7 micron, 1 micron, 2 microns, 5 microns, 10 microns or larger in diameter or cross-section. The average area occupied by a bead, and in turn the average size of a feature created from a bead in the methods set forth herein, can be, for example, at most about 1000 $\mu m^2$, 500 $\mu m^2$, 100 $\mu m^2$, 50 $\mu m^2$, 25 $\mu m^2$, 5 $\mu m^2$, 1 $\mu m^2$, 0.5 $\mu m^2$, 0.1 $\mu m^2$ or smaller. If desired, the variation between the area occupied by the beads may be tightly controlled, for example less than 25%, less than 10%, less than 5%, less than 2% or less than 1%.

Single stranded templates which are immobilized through their 5' end regions to beads are available for hybridization through their 3' end regions. If the templates have been amplified on the beads, then the sequence complementary to the 3' end region of the template may be known, for example, if the 3' sequence is derived from one of the adapters attached to the target fragments during an amplification step. The 3' end region sequence may also be known if it has been synthesized as part of the bead-attached template. A surface to which beads are to be immobilized can, therefore, carry a primer sequence complementary to the 3' end regions of the bead-attached templates.

A surface that is contacted with beads in a method according to certain embodiments of the invention can include more than one different immobilized primer species. For example, a surface can have 2, 3, 4, 5 or more different primer species attached thereto. In some embodiments, one or more of the immobilized primers on a surface may carry a cleavable moiety that can be used to invert a template strand on the surface, for example, in a paired-end sequencing method as set forth in further detail elsewhere herein or as described in co-pending applications U.S. Ser. No. 11/973,321, which stems from WO 08/041,002, the contents of which are incorporated herein by reference in their entirety.

Beads can be immobilized to a surface by hybridization of a bead-attached template to a surface-attached primer, and such a device is one embodiment of the invention. The invention may involve a device including an array of beads on a surface wherein the beads are immobilized via hybridization to one or more oligonucleotide primers on the surface. The surface may be a cross-linked polyacrylamide hydrogel, as described below, to which thiophosphate modified priming sequences are attached, as shown below and in the examples section.

A method of the invention can include a step of primer extension in which a surface-attached primer is extended using a bead attached nucleic acid as a template. The term "primer extension" means making a first nucleic acid molecule (i.e., the primer) longer by fabricating a copy of a template sequence of a nucleic acid that is hybridized to the first nucleic acid molecule. A single strand can be turned into a double strand by hybridizing a short sequence at one end, and extending the short sequence. The extension can be performed using a polymerase and nucleoside triphosphates, or a ligase and a set of oligonucleotide cassettes of variable sequence. Primer extension can be carried out from a universal primer which hybridizes to a sequence common to multiple different nucleic acid templates, or can be carried out from a specific primer that hybridizes to a sequence that is unique to a particular template among different templates in a sample.

Figure 2:
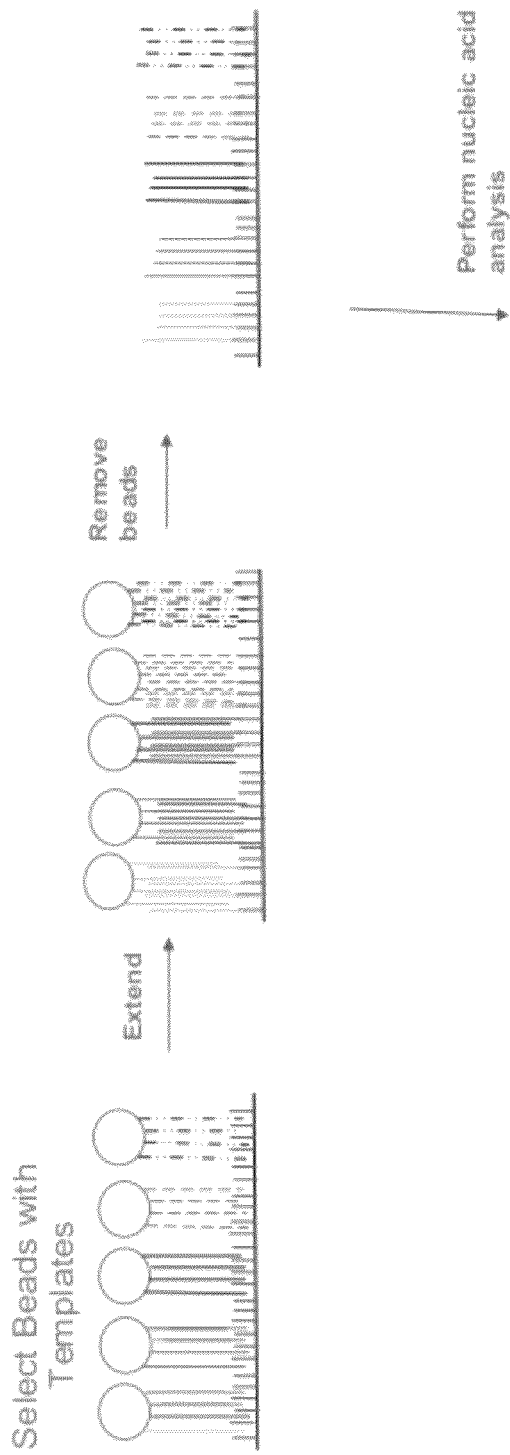
FIG. 2 shows a schematic of an embodiment of the invention where the beads are arrayed onto the surface via hybridization, and the templates copied.

An exemplary method that uses primer extension to fabricate an array of nucleic acids is shown in FIG. 2. In this embodiment beads having attached templates can be selected by hybridization of the templates to primers attached on the surface of another substrate. Beads that do not have templates that complement the surface-attached primers will not be immobilized and can be washed away. The primers on the surface can be extended using a nucleic acid polymerase and nucleotide triphosphates. Any nucleotide polymerase may be used including, for example, Taq polymerase, or Phusion DNA polymerase which is a high fidelity polymerase giving rise to fewer errors in the template strand.

The invention may thus in certain embodiments involve a composition including an array of beads on a planar surface wherein the beads are immobilized via hybridization to one or more oligonucleotide primers on the planar surface, and a nucleic acid polymerase. The polymerase may be present in solution, and/or bound to the primer/template sequences on the surface. The composition may further include one or more nucleoside triphosphates. The composition may further include four nucleoside triphosphates, which may be deoxynucleoside triphosphates.

In embodiments wherein one or more template nucleic acids are transferred from a bead to a surface by primer extension, conditions for producing no more than a single copy of each template molecule can be used. Alternatively, the templates can be copied by repeated cycles of hybridization, extension and denaturation. This can provide the advantage of creating localized sites of amplification on a surface. For example, if the surface carries primers that are complementary to the template nucleic acids but does not carry a primer that is complementary to the extended template, then the amplification can be localized at the bead-surface interface. More specifically, if the surface to which the beads are immobilized carries a single type of primer (i.e., having the same sequence, albeit in multiple copies), the extended copies can not be amplified solely on that surface because a second primer complementary to the extended copies is not present. In this example, since the DNA templates possess two distinct amplification sequences at their two ends, they cannot spread out across the first surface by bridge amplification; however the templates and their complementary copies can be further amplified via hybridization to complementary primers on the surface and on the beads such that a given template molecule is copied two or more times. In this way multiple copies of the template are transferred to the surface within the interface area of the bead.

It has been found that double-stranded extension products formed at a bead-surface interface can be denatured for further amplification, surprisingly, without resulting in migration of beads away from the interface position, even under conditions where chemical denaturing agents are delivered to the bead-surface interface via fluid flow. Once the bead and surface are brought in close proximity, amplification regions where the two surfaces overlap are created. Amplification can take place where the two surfaces are in close proximity and therefore both primers are present and conditions can be used, for example, by appropriate primer choice as set forth above, such that copies are present only on the location of the surface that is in close proximity to a bead. In this way, the density of molecules per unit area can be increased by performing one or more amplification cycles without the consequent increase in diameter of the resulting feature on the surface.

Cycles of primer hybridization, extension and denaturation used to transfer a nucleic acid from a bead to a surface can generally be carried out as set forth herein in regard to amplification methods. For example denaturation can be achieved by thermocycling, exposure to chemical denaturants or action of strand separating enzymes. Any number of desired cycles of primer hybridization, extension and denaturation can be carried out including, for example, at least 2, 5, 10, 20, 25, 50 or more.

Beads may be removed from contact with a surface after transfer of content to the surface, or after the optional amplification of the copied material. Returning to the example shown in FIG. 2, the beads can be removed after templates on the beads have been copied by extension of surface-attached primers. In embodiments wherein the beads are only immobilized via hybridization a protocol involving denaturation, such as heat or chemical treatment with formamide or hydroxide can be used to remove the beads from the surface to leave an array of extended templates on the surface. The resulting array can be used in a nucleic acid analysis method such as those described elsewhere herein.

Templates that are present on a collection of beads may comprise a pool of nucleic acid fragments from a biological source, or may comprise a pool of synthesized oligonucleotides. The biological source can be a eukaryotic unicellular or multicellular organism. Exemplary eukaryotic organisms that are particularly useful include, without limitation, a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog; a *dictyostelium discoideum*; a fungi such as yeast; or a plasmodium falciparum. The biological source can also be an organism having a smaller genome such as a prokaryote, an archae, a virus, or a viroid.

References herein to a particular nucleic acid sequence may, depending on the context, also refer to nucleic acid molecules which comprise the nucleic acid sequence. Sequencing of a target fragment means that a read of the order of bases is determined. The bases do not need to be contiguous, although this may be preferred, nor does every base on the entire fragment have to be sequenced. Sequencing using cycles of ligation where more than a single base varies between the ligation cassettes is within the scope of certain herein disclosed embodiments of the invention, and hence every cycle of sequencing does not have to result in determination of a base for that cycle.

After content has been transferred from beads to a surface, the resulting features can be modified, for example, to facilitate subsequent uses such as detection of the transferred content. For example, after bead-attached templates have been copied onto the surface of an array, the resultant nucleotide features can be further amplified on the surface. This can be advantageous if insufficient material has been transferred from the beads. This may allow the use of smaller beads, which carry less material. In such instances, the features after amplification may be larger than the original beads. Amplification can be carried at the features of an array using methods exemplified above with regard to amplifying nucleic acids on the surface of beads. However, amplification need not be carried out for nucleic acids in features of an array after the nucleic acids have been copied or otherwise transferred from beads.

Nucleic acids that are present in features that have been fabricated using a bead-based transfer method set forth herein can be used for any of a variety of functions. Exemplary functions include, but are not limited to, serving as a hybridization probe for a complementary nucleic acid target, serving as a primer for enzymatic extension, serving as a ligation probe, serving as a template for an enzymatic extension or ligation reaction, or serving as a substrate for a nucleic acid binding molecule such as a DNA binding protein or enzyme. It will be understood that the functions of a nucleic acid can change during different steps of a method set forth herein. Accordingly, the nomenclature used to refer to a nucleic acid in one step may not necessarily limit the functions of the nucleic acid, or a copy thereof, with regard to other steps. For example, a nucleic acid can be referred to as a template during a copying step and this template or its copy can subsequently serve as a primer or probe in another step. Exemplary methods that exploit various functions of the nucleic acid features fabricated by bead-based transfer methods are set forth in greater detail below.

An array of nucleic acid features fabricated using the methods set forth herein may be further used in a number of biological assays including, for example, nucleic acid detection techniques such as genotyping, gene expression analysis, methylation analysis or sequencing. Exemplary nucleic acid detection techniques that can be used are described below. It will be understood that a nucleic acid that is attached to an array is often referred to as a "probe" and a nucleic acid that is detected by the probe is often referred to as a "target." However, this is merely a convention for ease of description and the terms can be used interchangeably with regard to the species of nucleic acid that is attached to an array feature and the nucleic acid that is detected at an array feature. Accordingly, the description set forth herein with regard to arrays of templates or target nucleic acids are relevant to arrays of probes and vice versa.

Arrays that have been fabricated using beads are particularly useful for multiplex detection of nucleic acids due to the high density of probes present on the arrays. The presence or quantity of particular sequences in a sample can be determined, for example, based on hybridization specificity between the particular sequences and the probes present on an array. If desired, nucleic acid samples can be amplified prior to being contacted with an array, for example, using PCR methods, rolling circle amplification methods, random prime amplification methods or the like, in order to prepare copies of target nucleic acids in the sample.

A sample bearing target sequences can be contacted with an array of probes under conditions where target sequences hybridize to complementary probes and the hybrids can be detected to determine the presence or quantity of target nucleic acids in the sample. Array based detection of hybrids can be carried out using methods known in the art such as those described in U.S. Pat. No. 6,355,431; US 2003/0211489, or US 2005/0181394, each of which is incorporated herein by reference. Thus, multiplex detection methods can be used to detect the presence of target nucleic acids having specific sequences or to quantitate the number of such target nucleic acids in a sample, for example, as in expression analysis.

In particular embodiments, target sequences can be detected in a sample based on target-specific modification of probes or primers. Target-specific modifications include any modification of a primer or probe that is indicative of a specific sequence present in a target nucleic acid that hybridizes to the probe. Examples of target-specific modifications include, for example, enzymatic modifications of primers and probes such as polymerase directed primer extension and ligase catalyzed ligation of probe ends. Such methods are described in further detail below in the context of genotyping reactions, but can be used for other purposes as well. The examples below are described in the context of reactions involving a probe occurring at a feature on an array. However, it will be understood that a probe or primer can instead be modified, for example in solution or on a separate solid phase substrate, and the modified probe can subsequently be detected at an array feature. Thus, probe or primer modification need not occur on the array where detection occurs.

Multiplex detection methods can involve detection at a resolution that allows single nucleotide polymorphisms (SNPs) to be distinguished. Extension assays are useful for detection of alleles, mutations or other nucleic acid features at the resolution of SNPs, for example, to determine genotypes. Extension assays are generally carried out by modifying the 3' end of a first nucleic acid when hybridized to a second nucleic acid. In embodiments where a target nucleic acid is hybridized to a surface attached probe, either the probe nucleic acid can be extended using the target nucleic acid as a template or the target nucleic acid can be modified using the probe as a template.

Exemplary primer extension approaches that can be used include, for example, allele-specific primer extension (ASPE) and single base extension (SBE). Briefly, SBE utilizes an extension primer that hybridizes to a template nucleic acid at a location that is proximal or adjacent to a detection position, the detection position being indicative of a single nucleotide polymorphism in the template. A polymerase can be used to extend the 3' end of the primer with a nucleotide analogue labelled with a detection label. ASPE is an extension assay that utilizes extension primers that differ in nucleotide composition at their 3' end. Template-directed modification of the 3' portion of the primer, for example, by polymerase directed addition of a labelled nucleotide yields a labelled extension product if the template includes the target sequence. The presence of the labelled nucleotide in the extended primers from an SBE or ASPE reaction can be detected at a particular location in an array and the added nucleotide identified to determine the identity of a single nucleotide polymorphism. Another primer extension method that can be used for multiplex detection on arrays is pyrophosphate detection, which is described below in further detail in the context of sequencing applications. SBE, ASPE and pyrophosphate based genotyping detection can be carried out as described, for example, in US 2003/0108867; US 2003/0215821; US 2003/0108900 or US 2005/0181394, each of which is incorporated herein by reference.

Multiplex detection with arrays can also include a ligation assay such as oligonucleotide ligation assay (OLA) or ligation of pre-circle probes to form circular probes. Ligation assays involve the template-dependent ligation of two probe ends. In embodiments where a target nucleic acid is hybridized to a surface attached probe, either the surface attached probe can be ligated to a second probe using the target nucleic acid as a template or an end of a target nucleic acid can be ligated to a second probe end using the surface attached probe as a template. In embodiments where the probe ends hybridize directly adjacent to each other, covalent linkage can occur via a ligase. Alternatively, an extension-ligation assay can be used wherein hybridized probe ends are non-contiguous and one or more nucleotides are added along with one or more agents that join the probe ends via the added nucleotides. A ligation assay or extension-ligation assay can be carried out with two separate probes that become ligated together, or the assay can be carried out with a single padlock probe that is ligated to become circular. A label incorporated into a ligated product can be detected at an array feature to determine the presence of a single nucleotide polymorphism or other nucleic acid sequence characteristic. Exemplary conditions for ligation assays or extension-ligation assays are described, for example, in U.S. Pat. No. 6,355,431 and US 2003/0211489, each of which is incorporated herein by reference.

In particular embodiments, modified probes such as ligation products can include priming sites configured to allow amplification of the modified probe product using primers that hybridize to the priming sites, for example, in a PCR reaction or rolling circle reaction. Universal priming sites are particularly useful. A modified probe such as a ligated probe can further include other features such as an adaptor sequence that is specific for a probe on an array, restriction site for cleaving the modified probe or a tag sequence as described, for example, in U.S. Pat. No. 6,355,431 and US 2003/0211489, each of which is incorporated herein by reference.

An array fabricated by the methods set forth herein can also be used to detect methylation of nucleic acids. In particular embodiments, methylated cytosines can be distinguished from non-methylated cytosines based on their differential reactivity with bisulfite in which case the latter are converted to uracil and the former are protected from conversion. Nucleic acids in a sample that has been treated with bisulfite can be detected using arrays as exemplified herein for detecting single nucleotide polymorphisms or the nucleic acids can be sequenced on arrays. Array detection is used to distinguish whether a uracil is present at site expected to be cytosine, which is indicative of unmethylated cytosine in the original sample, or whether a cytosine is present at such a site, which is indicative of a methylated cytosine in the original sample. Alternatively, methylation can be detected using arrays to distinguish different fragments resulting from treating a nucleic acid sample with methylation sensitive restriction endonucleases. Useful methods for detecting methylation of nucleic acids with arrays are described, for example, in US 2003/0170684, which is incorporated herein by reference.

The invention also encompasses methods of determining the identity of one or more bases in the features derived by copying the templates on the beads. The features on the surface may be identified using cycles of hybridization and stripping of labelled oligonucleotides. The array of known sequences may be further used to analyze a biological sample at certain positions in the sample.

The invention also encompasses, according to certain embodiments, methods of sequencing nucleic acid features that have been fabricated using methods set forth herein. For example, these and related invention embodiments provide a method of nucleic acid sequencing comprising amplifying a pool of nucleic acid templates on beads as described above, transferring the sequences to another surface by transferring or copying the templates and carrying out a nucleic acid sequencing reaction to determine the sequence of the whole or a part of at least one nucleic acid feature on the surface.

Sequencing can be carried out using any suitable sequencing technique, wherein nucleotides are added successively to a free 3' hydroxyl group, resulting in synthesis of a nucleic acid chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also useful, as are techniques using detection of pyrophosphate release (pyrosequencing). It will be understood that sequencing can proceed in a 3' to 5' direction, for example, in embodiments that utilize sequencing by ligation.

The initiation point for a sequencing reaction may be provided by annealing of a sequencing primer to a target nucleic acid present at a feature of an array. In this connection, a known adapter region that is present on a target nucleic acid, for example, as a result of an amplification reaction described previously herein, can be used as a priming site for annealing of a sequencing primer.

In a particular embodiment, a nucleic acid sequencing reaction can include steps of hybridizing a sequencing primer to a single-stranded region of a linearized amplification product, sequentially incorporating one or more nucleotides into a nucleic acid strand complementary to the region of amplified template strand to be sequenced, identifying the base present in one or more of the incorporated nucleotide(s) and thereby determining the sequence of a region of the template strand.

One preferred sequencing method which can be used in accordance with the invention relies on the use of modified nucleotides having removable 3' blocks, for example, as described in WO 04/018497 and U.S. Pat. No. 7,057,026, the contents of which are incorporated herein by reference in their entirety. Once the modified nucleotide has been incorporated into the growing nucleic acid chain complementary to the region of the template being sequenced there is no free 3'-OH group available to direct further sequence extension and therefore the polymerase can not add further nucleotides. This allows convenient detection of single nucleotide incorporation events. Once the identity of the base incorporated into the growing chain has been determined, the 3' block may be removed to allow addition of the next successive nucleotide. By ordering the products derived using these modified nucleotides, it is possible to deduce the DNA sequence of the DNA template. Multiple reactions can be done in parallel on a single array, for example, if each of the modified nucleotides has a different label attached thereto, known to correspond to the particular base, thereby facilitating discrimination between the bases added during each incorporation step. If desired, a separate reaction may be carried out for each of the modified nucleotides.

Modified nucleotides used in an amplification or sequencing reaction may carry a label to facilitate their detection. A fluorescent label, for example, may be used for detection of modified nucleotides. Each nucleotide type may thus carry a different fluorescent label, for example, as described in U.S. Provisional Application No. 60/801,270 (Novel dyes and the use of their labelled conjugates), published as WO 07/135,368, the contents of which are incorporated herein by reference in their entirety. The detectable label need not, however, be a fluorescent label. Any label can be used which allows the detection of an incorporated nucleotide. Similarly, fluorescent labels or other labels can be used to detect any of a variety of analytes on an array fabricated using a bead-based transfer method set forth herein.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Application No. 60/788,248 (Systems and devices for sequence by synthesis analysis), published as WO 07/123,744, which entered the U.S. national phase as U.S. patent application Ser. No. 12/295,337, each of which are incorporated herein by reference in their entirety. Detectors that are capable of obtaining an image of an array surface such as those configured to scan an array surface. Such detectors can be configured to take a static image of an array surface, scan a point across an array surface or scan a line across an array surface. Exemplary scanning devices that can be used are described, for example, in U.S. Pat. No. 7,329,860, which is incorporated herein by reference. A detector can be configured to obtain an image of an array at high resolution, for example, in the low micron to submicron range. In particular embodiments, an image can be obtained at a Rayleigh resolution between 0.2 and 10 micrometers.

The invention is not intended to be limited to use of the sequencing methods outlined above, as a variety of sequencing methodologies which utilize successive incorporation of nucleotides into a nucleic acid chain or removal of nucleotides from a nucleic acid chain can be used. Suitable alternative techniques include, for example, Pyrosequencing FISSEQ (fluorescent in situ sequencing), MPSS and sequencing by ligation-based methods, for example as described in U.S. Pat. No. 6,306,597. Sequencing by hybridization methods can also be used.

A nucleic acid may be analyzed to obtain a first and then a second sequencing read from opposite ends of the nucleic acid. Methodology for sequencing both ends of nucleic acids at array features (also referred to as "clusters") are described in co-pending applications WO 07/010,252, which entered the US national phase as U.S. patent application Ser. No. 11/989,172 and WO 08/041,002 and U.S. 2009/0088327, the contents of which are incorporated by reference herein in their entirety. These methods utilize a step of copying a first template strand by hybridizing the 3' end to an immobilized primer followed by extending the resulting bridged structure to generate a second template strand. This copying step can be carried out after the template has been sequenced from a first end. Then the first strand can be cleaved from the surface and the remaining second template strand can be sequenced from the other end. In order to practice this embodiment of the invention, two or more immobilized primers are utilized, at least one of which is configured to be cleavable in order to release the first template strand.

One or more of the sequencing reads may be carried out on the layer of beads while the beads are in contact with the surface. In particular embodiments, the nucleic acid material on the beads can be sequenced in situ either before or after the nucleic acid material is transferred to the surface. Alternatively, the nucleic acid material on the beads can be sequenced in situ and the material need not be transferred to the surface at all.

Taking as an example an embodiment where nucleic acid material is sequenced in situ either before the material is transferred to the surface, the beads may carry templates which are used to capture the beads by hybridization, and the templates copied to the surface by extension. The beads may carry additional single stranded template copies which did not hybridize to the support bound primers, and thus remain single stranded and available for sequencing. A first sequencing read may therefore be carried out on the beads using the bead immobilized templates and a non-immobilized primer hybridized to the templates. The beads may then be removed from the support, for example by denaturing the duplexes produced by the initial extension, to leave an array of features which are single-stranded copies of the templates on the beads. The features on the array may then be sequenced to generate a second read. The first read on the bead, and the second read on the array may originate from opposite ends of the original templates, and thus provide paired read information from both ends of the templates.

With a significant proportion of human genomic DNA being composed of repetitive sequence, it can be beneficial to reduce the complexity of the sample in order to reduce the amount of sequencing required to identify particular sequences of interest. Furthermore, with prior genetic information, it is possible to correlate a phenotype, such as a predisposition to a disease, with the genetic variation of one or more regions of the genome. In some applications of genetics, what is desired is the application and advantages of high throughput sequencing methods specifically to particular regions of interest among many individuals. In addition, in certain circumstances, it is desirable to generate a 'genome-wide' analysis of a particular subset of genomic features, such as exons, chromosomes etc., in one or more individuals. For example genome-wide analysis of exons can be useful to correlate genetic diversity in the protein-coding regions across many individuals. Such analyses can be carried out using certain of the invention embodiments described herein in a number of ways, several of which are described below.

For example, a pool of different bead-bound oligonucleotides can be prepared in which a single oligonucleotide is attached to each individual bead. The oligonucleotides can be in the form of RNA or DNA. The bead can be used as bait in order to selectively hybridize to complementary sequences from solution. The hybridized material can be copied on the beads using, for example, methods described herein previously. The beads can then be contacted with a surface such that the ends of the copied material hybridize to surface-attached primers and then copies of the bead bound material can be made by extension of the primers.

Alternatively two or more primer sequences can be attached to each bead, and the beads used to selectively bind to flanking regions of target sequences such that the primers can be used to amplify the region of a target nucleic acid that resides between the flanking primer binding sites. This negates the need for emulsion amplification, as the amplification on each bead is sequence selective, and avoids diffusion of templates between beads since the priming sequences are different between different beads. If the primers also have a universal region at the 5' ends, then the ends of the different amplified sequences will be the same, and thus amenable to capture on a surface carrying a single primer species.

Templates that are present on beads may be amplified from a pool of chemically synthesized oligonucleotides. Thus the beads may begin with a single primer species attached to all the beads, but if a collection of oligonucleotide probes is prepared which have universal ends complementary to the primers on the beads and variable central portions, then individual oligonucleotide molecules can be amplified on beads in the same way as individual strands of nucleic acid strands from a biological source. The oligonucleotide amplicons can be captured onto the surface and used to form a high density array of nucleic acid features. These features can have their sequences decoded by cycles of hybridization using labelled nucleic probes. Once the features are determined, they can be used for sequencing or genotyping as described above.

An array fabricated by a method set forth herein can be used to capture target sequences by hybridization. The captured target sequences can then be amplified using the sequences copied from the beads as amplification primers. As the transfer from the beads gives nucleic acid sequences at discrete locations, if the captured sequences are amplified, they are unable to spread outside the area of the feature as the spaces between the features do not carry any amplification primers. A resulting advantage is the regular spacing of nucleic acid features on a surface that may be suitable for subsequent amplification. The nucleic acid features produced may comprise amplification primers, which may be of a single sequence per feature, or two or more sequences per feature. The sequences may be universal sequences common to all features, or may be different between different features. A further embodiment contemplates the use of the amplification primers on the surface for the amplification of template molecules. The amplified template molecules may comprise substantially all the primer sequences in the feature, as the amplification reaction can be pushed through a large number of cycles as the features are unable to spread into areas where there are no primers. Thus the amplified features may be of similar size and intensity to each other, as each feature will be grown from a similar number of primers which are fabricated on the surface using methods described herein.

Methods for bead-based transfer of content to a surface and related compositions are exemplified herein with regard to transfer of nucleic acid content for ease of description. However, it will be understood that other content can be used in the methods and compositions including, without limitation, proteins such as antibodies, enzymes or receptors; peptides; saccharides; synthetic molecules such as candidate enzyme cofactors, enzyme inhibitors, enzyme activators, enzyme substrates; drug candidates or the like. Useful enzymes include for example, kinases, phosphatases, proteases, nucleases, polymerases, lipases, reductases and others known in the art.

The invention is herein further described by reference to the following non-limiting examples.

EXAMPLES

The following are examples of general techniques which may be applied in carrying out the method of the invention.

Figure 3:
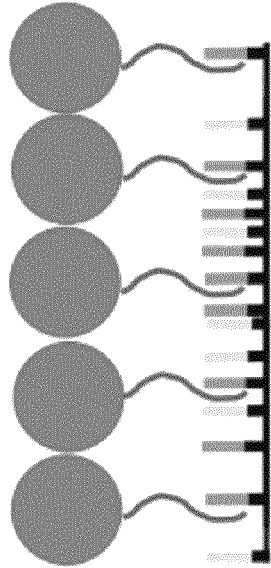
FIG. 3 shows a schematic of an exemplary method whereby templates on beads can be copied onto a surface. PCR products in solution were prepared using one biotinylated primer per reaction. The amplicons were captured onto one micron streptavidin beads and denatured to make the nucleic acids single stranded. The beads were then flushed into a flow cell and allowed to hybridize to the primers attached to the flow cell surface.

The following experiment, drawn as a cartoon in FIG. 3, shows the efficient transfer of material from a bead to a surface, removal of the beads, and cycles of sequencing to show that the transferred templates on the surface retain their sequence integrity and do not overlap.

1. Two PCR products (CT417 (SEQ ID NO: 5)) and CT418 (SEQ ID NO: 6)) were prepared as shown in FIG. 4.

The two products carried universal ends, and were prepared using a single pair of primers; namely:

```
Primer A (P7-OH):
                                         (SEQ ID NO: 1)
5'-CAAGCAGAAGACGGCATACGA Primer B (5' biotinylated-P5-SBS3):
                                         (SEQ ID NO: 2)
5'-biotin-AATGATACGGCGACCACCGAGATCTACACTCTTTCCCTA CACGACGCTCTTCCGATCxT
```

Where x=phosphorothioate.

Figure 5:
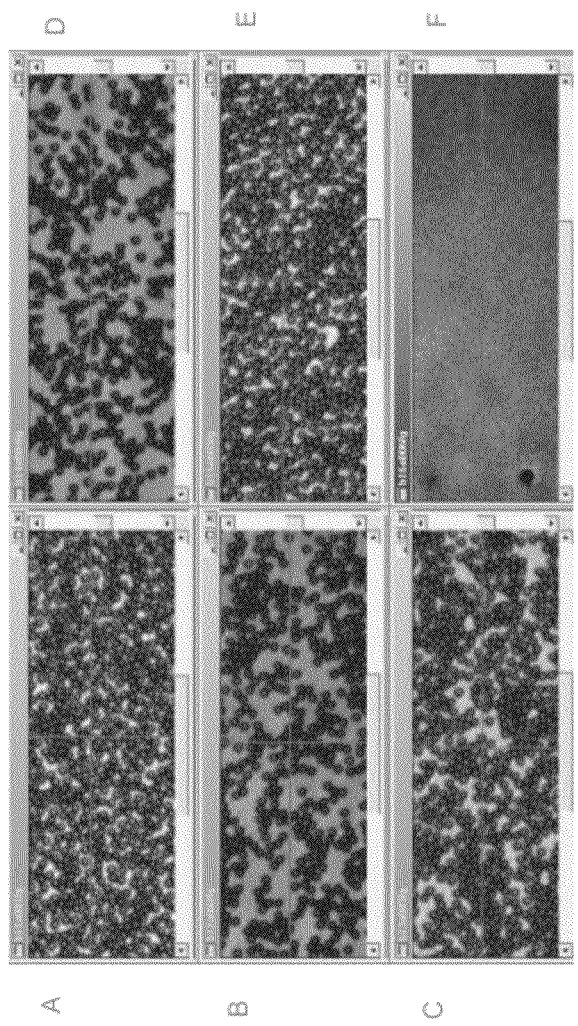
FIGS. 5A through 5F show white light optical images of surfaces after contact with various beads and washing to remove non-hybridized beads (panel A: beads prepared with CT417 (SEQ ID NO:5) template; panel B: beads prepared with CT418 (SEQ ID NO:6) template; panel C: a 1 to 1 mixture of beads prepared with CT417 template and beads prepared with CT418 template; panel D: a 1:4 mixture of beads prepared with CT417 template and beads prepared with CT418 template; panel E: beads prepared with a mixture of CT417 and CT418 templates; and panel F: blank beads with no template attached). As shown by the images beads carrying template sequences hybridize to the immobilized primers on the surface, whereas beads with no templates do not.

The template strands were amplified using a PCR reaction as follows:

Reagent solution:
1 µl (1/50) dilution of 10 nM stock DNA (CT417 or CT418)
Primer A, final conc 0.5 µM
Primer B, final conc 0.5 µM
25 µl Phusion HF 2× mastermix
$H_2O$ to final volume 50 µl
Cycled for 25 cycles of 94 C for 10 s; 65 C for 30 s; 72 C for 30 s; Final extension of 72 C for 5 min 2. The templates were bound to streptavidin beads as follows: (note: all manipulations of beads were done using a magnet)
 a. 20 µl of MyOne C1 beads (Dynal), were prewashed twice with 1×B/W buffer (Binding and Wash buffer, manufacturer's recommendation)
 b. Resuspended the beads in 25 µl of 2×B/W buffer and added 25 µl of biotinylated PCR product
 c. Incubated room temp for ~20 mins
 d. Pulled down beads, discarded supernatant and wash with 200 µl 1×B/W
 e. Washed again with 200 µl 1×B/W
 f. Washed with 200 µl Wash buffer (Illumina: 0.3×SSC/ 0.1% Tween)
 g. Made DNA bound to beads single-stranded by washing with 200 µl 0.1 N NaOH
 h. Pulled down, discarded denatured strand, and neutralized by washing with 200 µl Hybridization buffer (Illumina: 5×SSC/0.1% Tween)
 i. Washed again with 200 µl Hybridization buffer
 j. Transferred beads in Hyb buffer to fresh tubes
 k. Washed with 200 µl Wash buffer
 l. Resuspended beads in 20 µl Wash buffer 3. The beads from step 2 were flushed into the flowcell and printed as follows:
 a. Prepared a standard paired end flowcell (Illumina, San Diego, Calif.) (preparation of Illumina flow cells is described below, and in full in co-pending applications WO2008/002502 and U.S. application Ser. No. 11/973, 321 (corresponding to WO2008/041002), the contents of which are incorporated herein by reference in their entirety.
 b. Flushed through 120 µl of Hyb buffer at 60 µl/min, 20 C
 c. Increased temp to 96 C, pumped through a further 75 µl of Hyb buffer at 15 µl/min
 d. Cooled to 40 C
 e. Flushed through 75 µl of Wash buffer at 15 µl/min at 40 C
 f. Pumped a small air bubble into the lines (5 µl)
 g. Flushed in beads prepared in step 2 at 15 µl/min (10 µl beads per channel)
 h. Stopped pumping when the beads have filled the channels of the flowcell
 i. Incubated at 40 C for 10 mins
 j. Flushed out unbound beads with Wash buffer at 40 C, 15 µl/min for 75 µl
 k. Pumped in Taq extension mix (2 M betaine, 20 mM Tris, 10 mM Ammonium Sulfate, 2 mM Magnesium sulfate, 0.1% Triton, 1.3% DMSO, pH 8.8 plus 200 µM dNTP's and 25 units/mL of Taq polymerase (NEB Product ref M0273L)) at 15 µl/min for 75 µl
 l. Heated to 74 C for 90 s to copy strands from beads onto surface oligos
 m. Cooled to 60 C
 n. Removed beads from flowcell by flushing in formamide at 60 C, 15 µl/min for 75 µl, then 0.1 N NaOH at 20 C, 60 µl/min for 75 µl The features on the surface can be further copied using the following optional steps:
 o. Pump in Taq extension mix (same recipe as above), 60 µl/min for 75 µl
 p. Heat to 74 C for 90 s to create the $2^{nd}$ strand of each "bridge"
 q. SyBr Green stain and scan printed material Before the final removal step (step 2(n) above), beads were observed on the surface using a white light imaging system. Pictures of the beads in the flow cell are shown in FIG. 5. Beads without templates did not stick to the surface, showing that the capture was specifically via template hybridization (see FIG. 5F).

Figure 6:
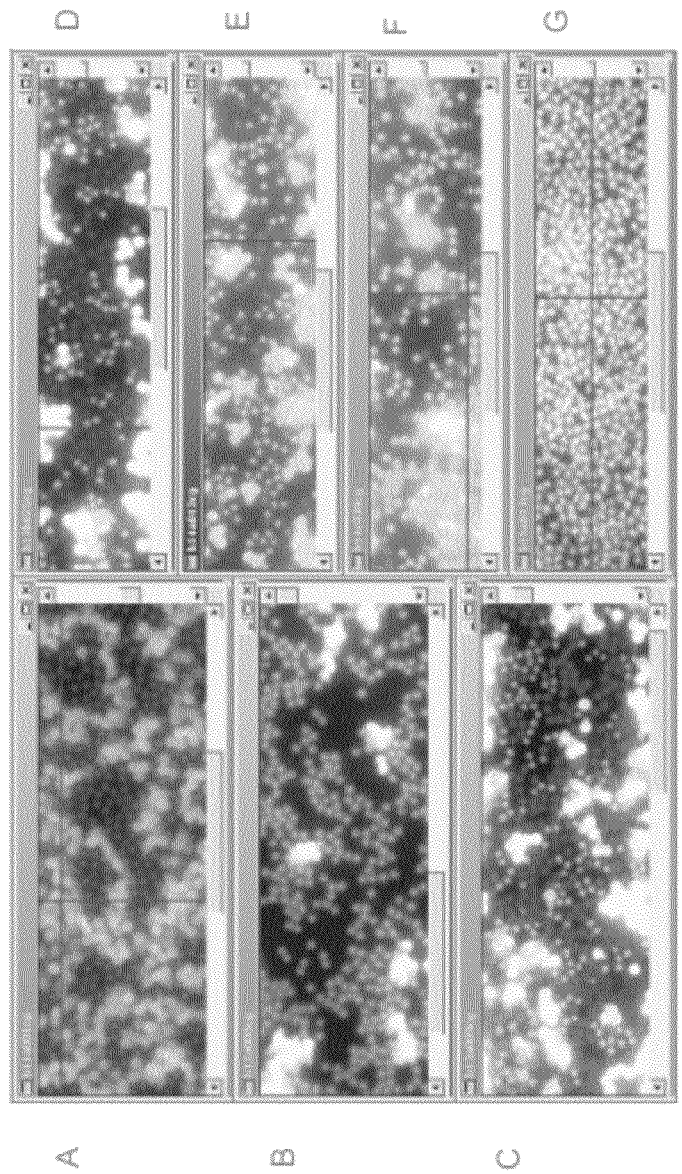
FIGS. 6A through 6G show first sequencing cycle images of beads marked in different shades of grey to represent different sequences (panel A: beads prepared with CT417 template; panel B: beads prepared with CT418 template; panels C and D: a 1 to 1 mixture of beads prepared with CT417 template and beads prepared with CT418 template; panels E and F: a 1:4 mixture of beads prepared with CT417 template and beads prepared with CT418 template; and panel G: beads prepared with a mixture of CT417 and CT418 templates). Beads with single templates show spots of a single grey intensity with no overlap between adjacent spots. Beads with different templates are shown as different intensity features. The ratio of beads in solution is reflected by the number of spots of the two intensities on the surface. Beads carrying mixed templates still show discreet spots, but at a single greyscale in every spot (viewed as a single color in the original image).
Figure 7:
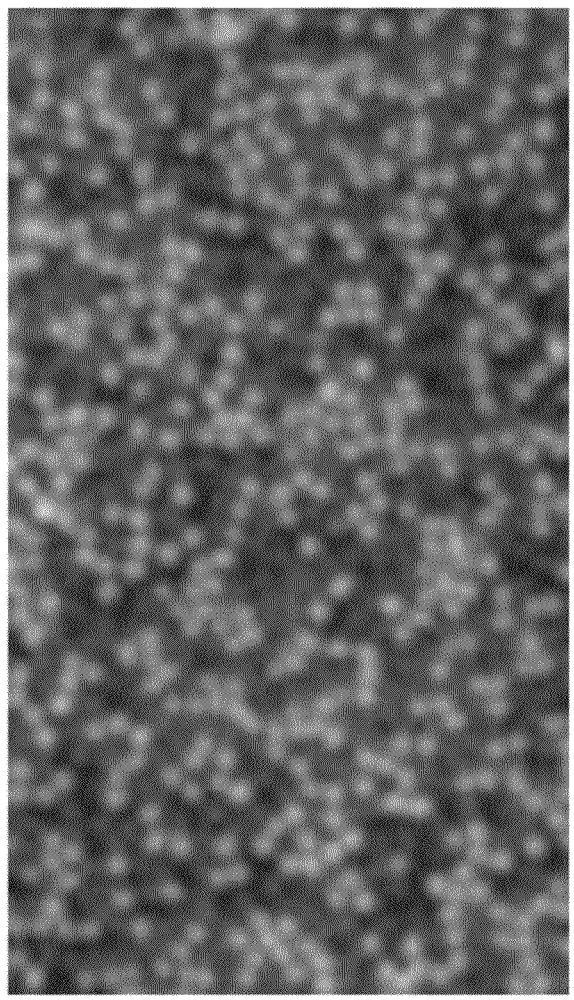
FIG. 7 shows a zoomed in version of a high density array of features fabricated using a 1:1 mixture of two different bead types, each bead type having a different attached template sequence. Both bead types had an average diameter of 1 micron. The image was obtained following replication of bead-bound templates to the array surface and removal of the beads. The features on the surface produce a single discrete grey color intensity, demonstrating that the templates on the beads can be copied onto the surface without overlap of adjacent sequences. Furthermore each spot is a similar size and intensity to other spots deriving from the same template.

FIG. 6 shows images of a number of channels of the flow cell which were hybridized with a primer complementary to the ends of the template and extended using a cycle of sequencing. Where the beads carried a single template, the appropriate nucleotide was incorporated. Mixtures of beads carrying monotemplates gave discrete regions of sequence at the appropriate ratio depending on the number of each bead types. Beads that carried a mixture of the two templates gave a mixture of both bases. FIG. 7 shows a high resolution image of features on a surface derived from a one micron bead. The features were tightly packed on the surface, and show discrete areas of non-overlapping signal, with each spot showing similar size and intensity.

The experiments detailed below show the conditions used for helicase-dependent amplification on a pool of beads:

3. Streptavidin beads were grafted with biotinylated primers A and B as follows (note: all manipulations of beads were done using a magnet):
   a. 80 μl of MyOne C1 beads (Dynal) were prewashed twice with 1×B/W buffer (Binding and Wash buffer, manufacturer's recommendation)
   b. Resuspended the beads in 100 μl of 2×B/W buffer+50 μl of primer A and 50 μl of primer B
   c. Incubated room temp for ~20 mins
   d. Pulled down beads, discarded supernatant and washed with 200 μl 1×B/W
   e. Washed again with 200 μl 1×B/W 4. The beads from step 3 were then hybridized to templates from step 1 and the attached primers extended as follows:
   a. Gel-purified PCR products from step 1 above (eluted in buffer EB (QIAGEN)) were taken, Tween20 added to 0.1% and denatured by heating to 98 C for 5 mins and snap chilling on ice
   b. Added 20×SSC to give a final concentration of 5×SSC in the sample
   c. Incubated the denatured DNA at 45° C. and add 10 μl of grafted beads from step 3
   d. Continued incubation at 45° C. for 15 mins
   e. Washed beads three times in 200 μl pre-warmed Wash buffer (0.3×SSC/0.1% Tween) at 45° C.
   f. Washed beads in 200 μl extension pre-mix (2 M betaine, 20 mM Tris, 10 mM Ammonium Sulfate, 2 mM Magnesium sulfate, 0.1% Triton, 1.3% DMSO, pH 8.8)
   g. Resuspended the beads in 100 μl Taq extension mix ((2 M betaine, 20 mM Tris, 10 mM Ammonium Sulfate, 2 mM Magnesium sulfate, 0.1% Triton, 1.3% DMSO, pH 8.8 plus 200 μM dNTP's and 25 units/mL of Taq polymerase (NEB Product ref M0273L))
   h. Transferred to 0.2 ml tubes and heat to 74° C. for 180 s
   i. Cooled to room temp and washed beads three times with 200 μl 0.1N NaOH to remove seeding strands
   j. Washed beads with 200 μl Hybridization buffer (5×SSC/0.1% Tween)
   k. Washed beads with 200 μl Wash buffer
   l. Washed beads with 200 μl extension pre-mix
   m. Washed beads with 400 μl extension pre-mix
   n. Resuspended in 50 μl tHDA mix (BioHelix)—1.75 μl 100 mM MgSO4 (3.5 mM final), 10 μl 5M betaine (1M final), 13.25 μl H$_2$O, 25 μl 2×tHDA mix
   o. Incubated at 64° C. for 3 hrs
   p. Washed beads with 200 μl Wash buffer Illumina standard paired end flow cells were prepared as described in outline below, and as described in full in co-pending applications WO 08/002,502 and U.S. application Ser. No. 11/973,321 (corresponding to WO 08/041,002), the contents of which are incorporated herein by reference in their entirety:

Glass 8-channel flow cells (Silex Microsystems, Sweden) were thoroughly washed and then coated for 90 min at 20° C. with 2% acrylamide containing ~3.9 mg/ml N-(5-bromoacetamidylpentyl) acrylamide, 0.85 mg/ml tetramethylethylenediamine (TEMED) and 0.48 mg/ml potassium persulfate ($K_2S_2O_8$). Flow cell channels were rinsed thoroughly before further use. The coated surface was then functionalized by reaction for 1 hour at 50° C. with a mixture containing 0.5 μM each of two primers (primers C and D shown below) in 10 mM potassium phosphate buffer pH 7. Grafted flow cells were stored in storage buffer (5×SSC) until required.

primer 'C':
(SEQ ID NO: 3)
5' PS TTTTTTTTTTAATGATACGGCGACCACCGAGAUCTACAC-3'
("PS" = 5'-thiophosphate; U = 2-deoxyuridine)

primer 'D':
(SEQ ID NO: 4)
5' PS TTTTTTTTTTCAAGCAGAAGACGGCATACGAGoxoAT-3',
("PS" = 5'-thiophosphate; "Goxo" = 8-oxoguanine)

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

As used herein, the term "each" when used in reference to a collection of items is intended to identify one or more individual items in the collection but does not necessarily refer to every item in the collection unless the context clearly dictates otherwise.

The invention claimed is:

1. A method of creating an array of features, comprising
   (a) providing a plurality of beads, wherein each bead in the plurality of beads comprises nucleic acid content;
   (b) contacting the plurality of beads with a surface to produce a layer of beads on the surface;
   (c) transferring the nucleic acid content from the beads to the surface to create an array of spatially discrete features on the surface, wherein each spatially discrete feature comprises nucleic acid content from a bead in the plurality of beads; and
   (d) performing an amplification reaction using the nucleic acid content at each of the discrete features on the surface, thereby producing a homogenous population of nucleic acids at each feature.

2. The method of claim 1, wherein the transferring comprises physically transferring nucleic acids from the beads to each of the spatially discrete features on the surface.

3. The method of claim 1, wherein the transferring comprises covalently attaching nucleic acids from the beads to each of the spatially discrete features on the surface.

4. The method of claim 1, wherein the transferring comprises non-covalently attaching nucleic acids from the beads to each of the spatially discrete features on the surface.

5. The method of claim 1, wherein a single nucleic acid molecule is transferred from each of the beads to each of the spatially discrete features.

6. The method of claim 1, wherein several copies of a single nucleic acid species are transferred from each of the beads to each of the spatially discrete features.

7. The method of claim 1, wherein the transferring comprises replicating a nucleic acid from each of the beads to form a copy of the nucleic acid at each of the spatially discrete features.

8. The method of claim 1, wherein the transferring comprises physically transferring a nucleic acid molecule from each of the beads to attach the nucleic acid molecule to each of the spatially discrete features.

9. The method of claim 1, wherein the nucleic acids that are transferred from the beads to the surface are single stranded.

10. The method of claim 1, wherein the nucleic acids that are transferred from the beads to the surface are double stranded.

11. The method of claim 1, wherein the array of spatially discrete features comprises an average center-to-center spacing that is equivalent to the diameter of the beads.

12. The method of claim 1, wherein the array of spatially discrete features comprises an average center-to-center spacing that is less than 100 μm.

13. The method of claim 1, wherein the surface is flat or planar.

14. The method of claim 1, wherein the surface comprises wells, depressions, pillars, ridges or channels.

15. The method of claim 1, further comprising removing the beads from the surface after the transferring of the nucleic acid content from the beads to the surface.

16. The method of claim 15, further comprising obtaining an image of the surface after removing the beads from the surface.

17. The method of claim 1, wherein the nucleic acid content comprises nucleic acid primers that are transferred from the beads to the surface and used as primers in the amplification reaction.

18. The method of claim 17, wherein different beads in the plurality of beads comprise primers having the same sequence.

19. The method of claim 17, wherein different beads in the plurality of beads comprise primers having different sequences.

20. The method of claim 17, wherein each of the beads in the plurality of beads comprises two amplification primers each having a different sequence.

21. The method of claim 1, wherein the nucleic acid content comprises nucleic acid templates that are transferred from the beads to the surface and used as templates that are copied in the amplification reaction.

22. The method of claim 1, wherein nucleic acid content on each bead comprise a nucleic acid molecule having (i) a universal sequence that is the same as the universal sequence on other beads in the plurality of beads and (ii) a region of sequence that is different from a region of sequence on the other beads in the plurality of beads.

23. The method of claim 1, wherein the amplification reaction is performed using a universal primer that is complementary to a universal sequence that is the same as the universal sequence on other beads in the plurality of beads.

24. The method of claim 1, wherein the amplification reaction uses primers attached to the surface.

25. The method of claim 1, further comprising sequencing nucleic acids in the homogenous population of nucleic acids at each feature.

26. The method of claim 1, further comprising hybridizing nucleic acid probes to nucleic acids in the homogenous population of nucleic acids at each feature.

27. The method of claim 26, further comprising detecting a label at features on the surface, wherein the label is attached to the probes or attached to the nucleic acids in the homogeneous population of nucleic acids.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Primer A (P7-OH)

<400> SEQUENCE: 1
caagcagaag acggcatacg a                                      21

<210> SEQ ID NO 2
<211> LENGTH: 58
<212> TYPE: DNA
<213> ORGANISM: Artificial Sequence
<220> FEATURE:

```
<223> OTHER INFORMATION: Primer B (5' biotinylated-P5-SBS3)
<220> FEATURE:
<221> NAME/KEY: modified_base
<222> LOCATION: 1
<223> OTHER INFORMATION: biotin

<400> SEQUENCE: 2
aatgatacgg cgaccaccga gatctacact ctttccctac acgacgctct tccgatct         58

<210> SEQ ID NO 3
<211> LENGTH: 39
<212> TYPE: DNA
<213> ORGANISM: Artificial Sequence
<220> FEATURE:
<223> OTHER INFORMATION: Primer C
<220> FEATURE:
<221> NAME/KEY: modified_base
<222> LOCATION: 1
<223> OTHER INFORMATION: chemically modified to have thiophosphate
<220> FEATURE:
<221> NAME/KEY: modified_base
<222> LOCATION: 33
<223> OTHER INFORMATION: n = 2-deoxyuridine

<400> SEQUENCE: 3
tttttttttt aatgatacgg cgaccaccga ganctacac                              39

<210> SEQ ID NO 4
<211> LENGTH: 34
<212> TYPE: DNA
<213> ORGANISM: Artificial Sequence
<220> FEATURE:
<223> OTHER INFORMATION: Primer D
<220> FEATURE:
<221> NAME/KEY: modified_base
<222> LOCATION: 1
<223> OTHER INFORMATION: chemically modified to have thiophosphate
<220> FEATURE:
<221> NAME/KEY: modified_base
<222> LOCATION: 32
<223> OTHER INFORMATION: 8-oxoguanine

<400> SEQUENCE: 4
tttttttttt caagcagaag acggcatacg agat                                   34

<210> SEQ ID NO 5
<211> LENGTH: 215
<212> TYPE: DNA
<213> ORGANISM: Artificial Sequence
<220> FEATURE:
<223> OTHER INFORMATION: PCR Product

<400> SEQUENCE: 5
aatgatacgg cgaccaccga gatctacact ctttccctac acgacgctct tccgatctct       60
cactcctggc agagggacgt gtgactagcc atgggcccct aggtctccag ttcctgggta      120
gcttgtattt ttgaacatct cctgtatatt agttagatcg gaagagcggt tcagcaggaa     180
tgccgagacc gatctcgtat gccgtcttct gcttg                                 215

<210> SEQ ID NO 6
<211> LENGTH: 180
<212> TYPE: DNA
<213> ORGANISM: Artificial Sequence
<220> FEATURE:
<223> OTHER INFORMATION: PCR Product
```

-continued

```
<400> SEQUENCE: 6
aatgatacgg cgaccaccga gatctacact ctttccctac acgacgctct tccgatcttg      60
ggcccgggag gagtttgccg gggaggagtg ggtttggaat cggggttaaa ggaaagagaa     120
gatcggaaga gcggttcagc aggaatgccg agaccgatct cgtatgccgt cttctgcttg     180
```